US011547196B2

(12) United States Patent
Cavazzuti et al.

(10) Patent No.: US 11,547,196 B2
(45) Date of Patent: Jan. 10, 2023

(54) DEVICE FOR APPLYING A COMPOSITION IN THE FORM OF AN EMULSION COMPRISING A FILM-FORMING AGENT AND NON-VOLATILE OILS

(71) Applicant: L'OREAL, Paris (FR)

(72) Inventors: Roberto Cavazzuti, Chevilly la Rue (FR); Florence Lahousse, Chevilly la Rue (FR); Emilie Henin, Chevilly la Rue (FR); Stephane Arditty, Chevilly la Rue (FR); Estelle Prud'homme, Chevilly la Rue (FR); Sylvie Guillard, Chevilly la Rue (FR); Virginie Mondon, Chevilly la Rue (FR); Marcel Sanchez, Clichy (FR); Audrey Thenin, Clichy (FR)

(73) Assignee: L'OREAL, Paris (FR)

( * ) Notice: Subject to any disclaimer, the term of this patent is extended or adjusted under 35 U.S.C. 154(b) by 23 days.

(21) Appl. No.: 16/089,206

(22) PCT Filed: Mar. 24, 2017

(86) PCT No.: PCT/EP2017/057125
§ 371 (c)(1),
(2) Date: Sep. 27, 2018

(87) PCT Pub. No.: WO2017/167669
PCT Pub. Date: Oct. 5, 2017

(65) Prior Publication Data
US 2019/0125058 A1    May 2, 2019

(30) Foreign Application Priority Data

Mar. 31, 2016   (FR) ..................... 1652847

(51) Int. Cl.
| A61K 8/06 | (2006.01) |
| A45D 34/04 | (2006.01) |
| A61K 8/34 | (2006.01) |
| A61Q 1/04 | (2006.01) |
| A61K 8/81 | (2006.01) |
| A61K 8/891 | (2006.01) |

(52) U.S. Cl.
CPC ............ *A45D 34/045* (2013.01); *A61K 8/064* (2013.01); *A61K 8/342* (2013.01); *A61K 8/8152* (2013.01); *A61K 8/891* (2013.01); *A61Q 1/04* (2013.01); *A61K 2800/544* (2013.01); *A61K 2800/87* (2013.01)

(58) Field of Classification Search
None
See application file for complete search history.

(56) References Cited

U.S. PATENT DOCUMENTS

| 5,007,442 A | 4/1991 | Hirzel |
| 6,539,950 B1 | 4/2003 | Gueret |
| 6,780,402 B1 | 8/2004 | Agostini et al. |
| 2012/0263662 A1 | 10/2012 | Iimura et al. |
| 2016/0331672 A1 | 11/2016 | Khachikian et al. |

FOREIGN PATENT DOCUMENTS

| CN | 102665668 | 9/2012 |
| EP | 0 756 864 A1 | 2/1997 |
| EP | 1 070 467 A2 | 1/2001 |
| EP | 3 015 251 A1 | 6/2015 |
| FR | 3015251 | 6/2015 |
| JP | A-2001-145515 | 5/2001 |
| JP | A-2008-114057 | 5/2008 |
| JP | A-2012-055375 | 3/2012 |
| WO | 2013/153528 | 10/2013 |
| WO | WO 2014/154701 A2 | 10/2014 |

OTHER PUBLICATIONS

International Search Report dated May 16, 2017 in PCT/EP2017/057125 filed Mar. 24, 2017.
Postiaux, S. et al., "Long lasting and meal resistance in lipsticks and lipcreams using silicone acrylate copolymers", Research Disclosure, Mason Publications, XP007136165, 2006, 5 pages.

*Primary Examiner* — Jessica Worsham
(74) *Attorney, Agent, or Firm* — Oblon, McClelland, Maier & Neustadt, L.L.P.

(57) ABSTRACT

A device for applying a cosmetic composition to the lips and a method thereof, the device includes an applicator member with a partially flocked applicator head, a container containing the composition which is in the form of an emulsion of water; a film-forming agent chosen from vinyl polymers comprising at least one carbosiloxane dendrimer-based unit; a non-volatile hydrocarbon-based oil; and a non-volatile phenyl silicone oil.

22 Claims, 10 Drawing Sheets

Figure 1:
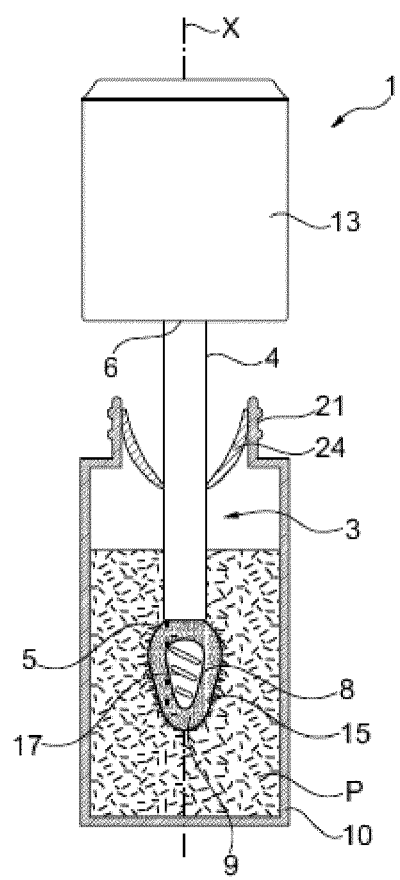

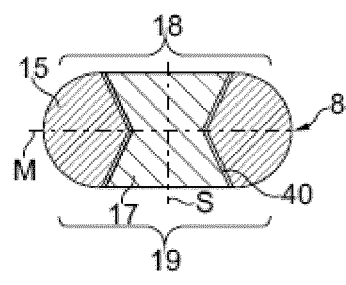
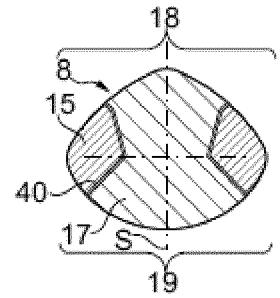
Fig. 22    Fig. 23
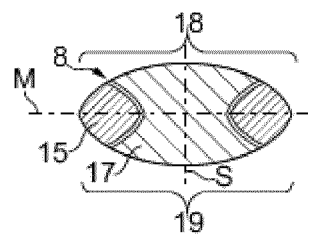
Fig. 24
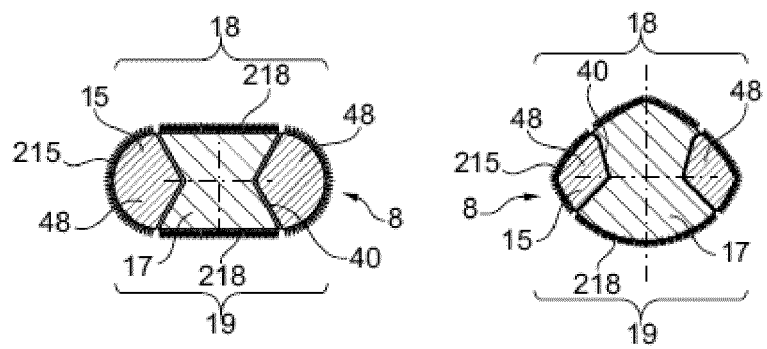
Fig. 25    Fig. 26

DEVICE FOR APPLYING A COMPOSITION IN THE FORM OF AN EMULSION COMPRISING A FILM-FORMING AGENT AND NON-VOLATILE OILS

The subject of the present invention is a device that is suitable for applying a composition in the form of an emulsion comprising a particular film-forming polymer, and also a process for making up and/or caring for the lips using the device and the composition.

The present invention relates to the field of making up and/or caring for the lips using fluid compositions.

The development of fluid compositions dedicated to making up and/or caring for the lips, such as liquid lipsticks, which are stable and endowed with satisfactory properties in terms of application (glidance on application, ease of spreading and fineness of the deposit), but also in terms of the makeup effect of the deposit on the lips, for instance the coverage and the absence of migration of the deposit, preferably without becoming tacky, is an ongoing objective.

Generally, formulations corresponding to anhydrous liquid galenical formulations conventionally comprise oils, which in particular provide gloss, optionally waxes for structuring the compositions, fillers, in particular for thickening the composition, film-forming polymers, and colorants.

In the more particular case of compositions providing coverage, it is important for the latter to be easy to apply to the lips, precisely and as an even layer. In addition, the deposit is not expected to migrate, which would result in the outline of the lips being made imprecise.

With the conventional lipstick compositions of this type, generally used with dipping applicators which have a flocked end piece, it is noted that the deposit is relatively thick, thereby giving it a more or less tacky nature, in particular induced by the use of these oils and of the polymers present. This nature is in particular reflected by a phenomenon of the made up lips sticking to one another, which is therefore unpleasant in terms of comfort for the user.

Another difficulty encountered with liquid lipsticks lies in the fact that the composition must be sufficiently fluid to be easily applied, but not too fluid, so as to avoid losing stability of the composition (pigment sedimentation) and losing ease of application (running and/or migration of the composition to the wrinkles and fine lines of the area around the lips).

Compositions which at the same time provide very good coverage of the lips, as a precise deposit, which does not migrate, and for which the tacky nature has been virtually dispensed with, and a device which would make it possible to apply them, are therefore sought.

These objectives are achieved by means of the present invention, a subject of which is thus a device for applying a cosmetic composition (P) to human keratin materials, in particular the lips, comprising:
- an applicator member (8) comprising a partially flocked applicator head (9),
- a container (10) containing the composition which is in the form of an emulsion comprising:
  - water;
  - at least one film-forming agent chosen from vinyl polymers comprising at least one carbosiloxane dendrimer-based unit;
  - at least one polar non-volatile hydrocarbon-based oil;
  - at least one non-volatile phenyl silicone oil, preferably without dimethicone fragment.

The invention also relates to a process for making up and/or caring for the lips, in which the abovementioned composition is applied to the lips by means of the abovementioned device.

Figure 2:
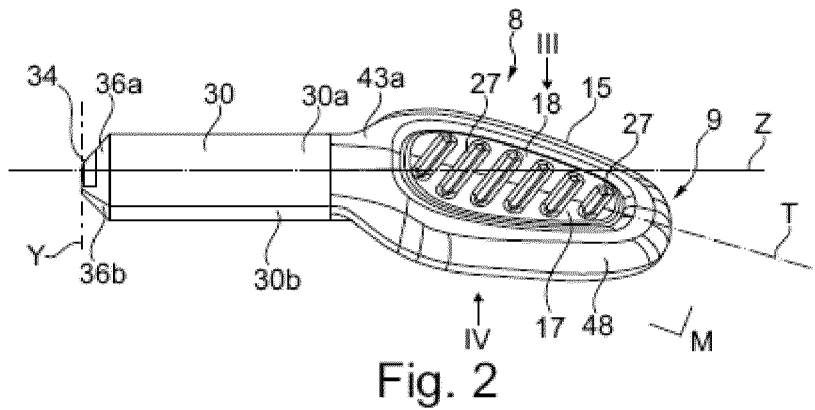
Figure 3:
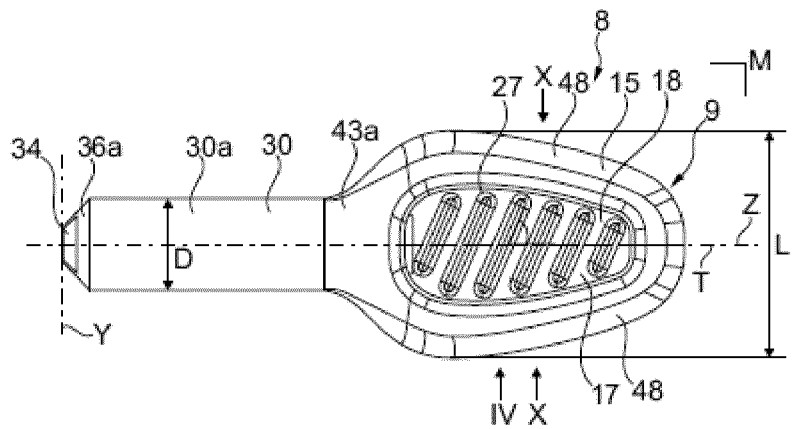
Figure 4:
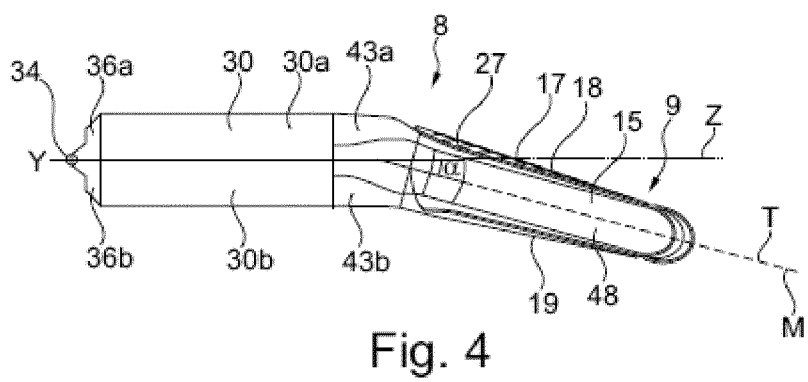
Figure 5:
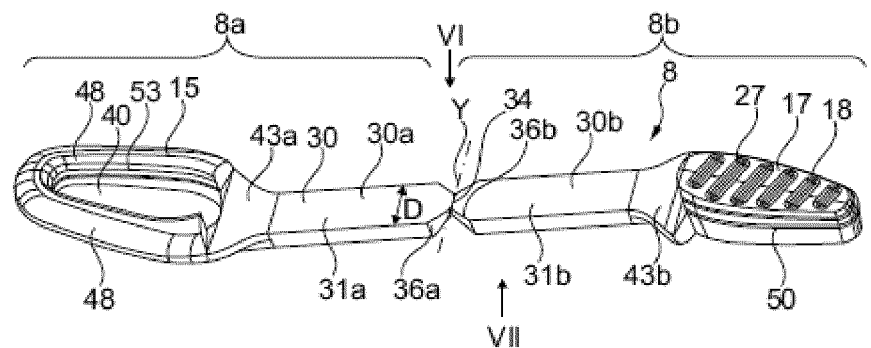
Figure 6:
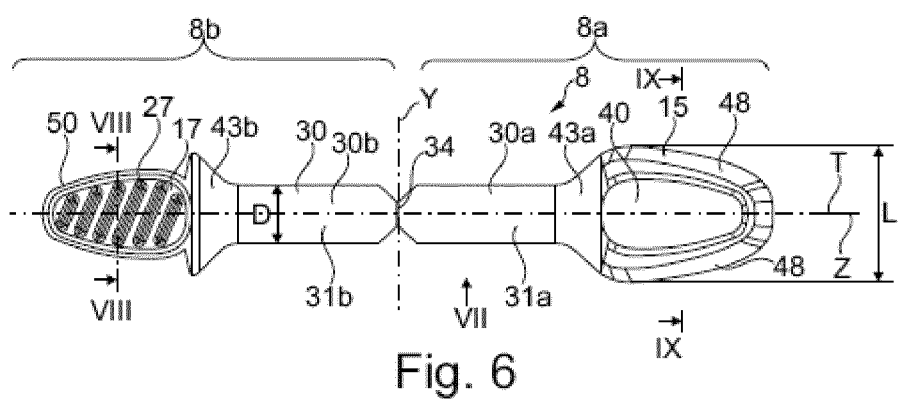
Figure 7:
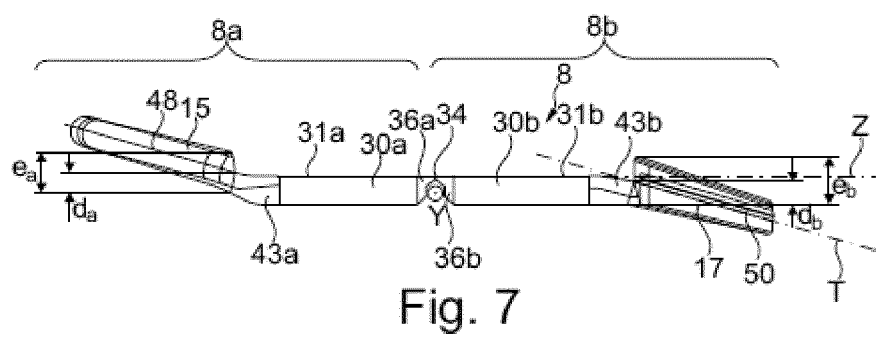
Figure 8:
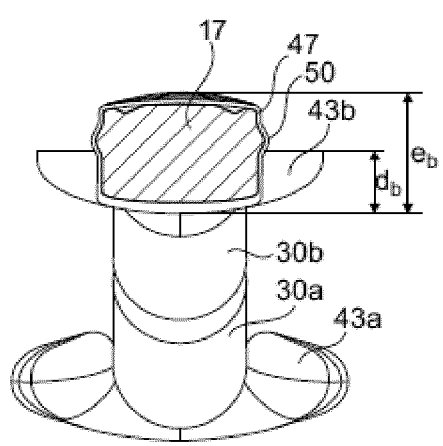
Figure 9:
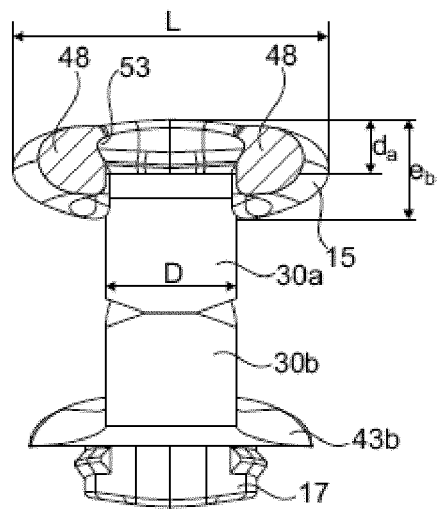
Figure 10:
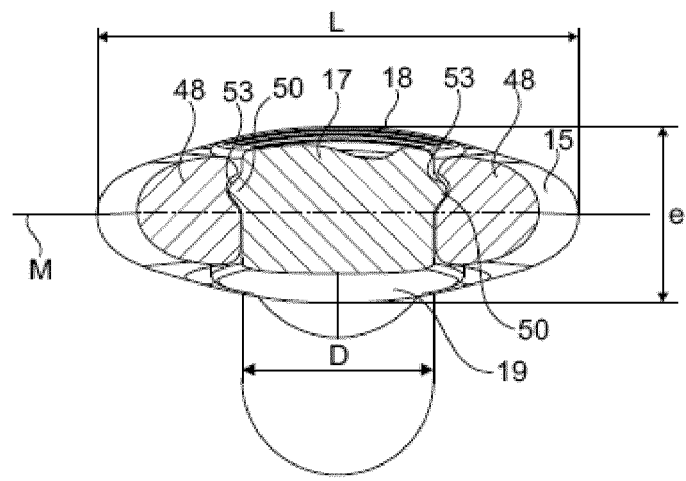
Figure 11:
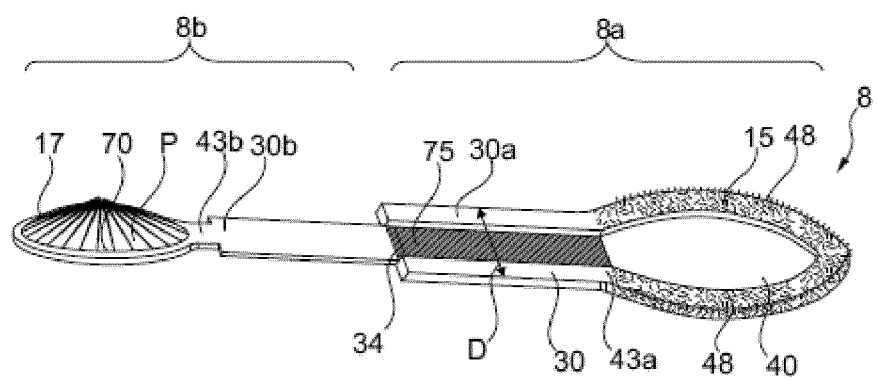
Figure 12:
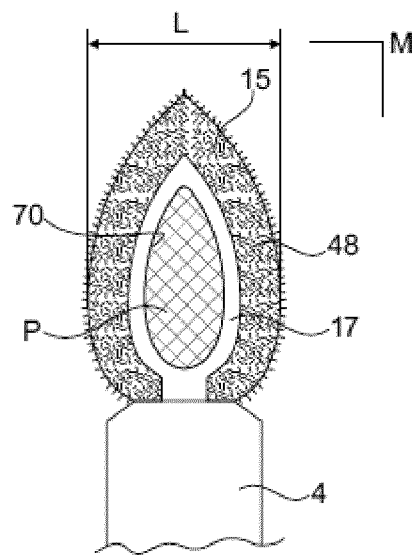
Figure 21:
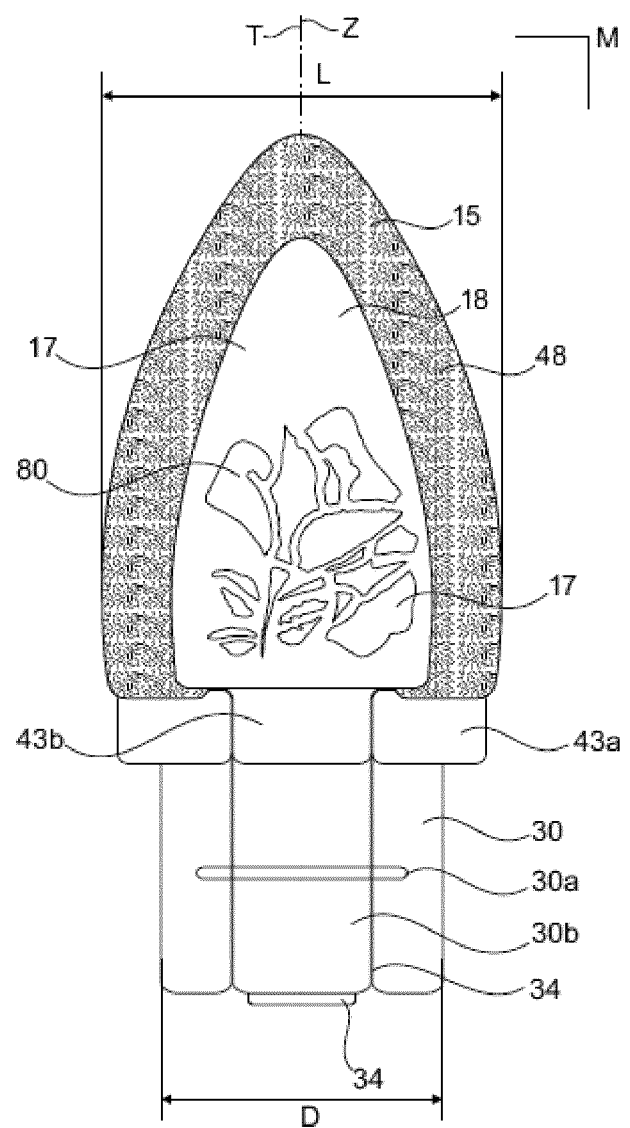
Figure 27:
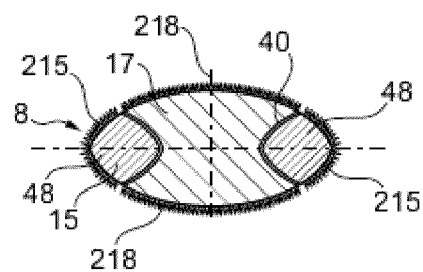
Figure 28:
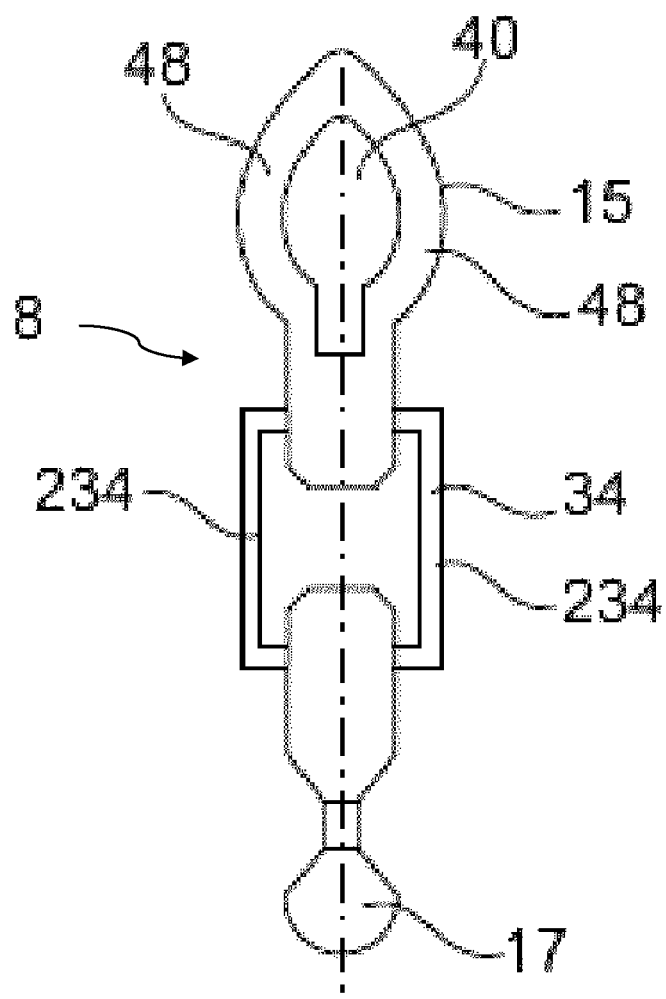

Application devices that are particularly suited to this composition will be described with reference to the appended drawings, in which:

FIG. 1 shows an example of a packaging and application device according to the invention, FIG. 2 schematically illustrates an example of an applicator member according to the invention, FIG. 3 shows a front view of the applicator member from FIG. 2, along III in FIG. 2, FIG. 4 shows a side view of the applicator member from FIGS. 2 and 3, along IV in FIG. 2, FIG. 5 shows the body of the applicator member from FIG. 2 in the open configuration, FIG. 6 illustrates a top view of the body of the applicator member from FIG. 5, along VI in FIG. 5, FIG. 7 shows a side view of the body of the applicator member from FIGS. 5 and 6, along VII in FIG. 6, FIG. 8 is a cross section on VIII-VIII in FIG. 6, FIG. 9 is a cross section on IX-IX in FIG. 6, FIG. 10 is a cross section on X-X in FIG. 3, FIG. 11 schematically illustrates a variant embodiment of the body of the applicator member, in the open configuration, FIG. 12 schematically and partially shows a front view of the applicator member from FIG. 11, following assembly, FIGS. 13 to 20 are schematic perspective views of variant embodiments of applicator members according to the invention, FIG. 21 shows a front view of another variant of an applicator member, FIGS. 22 to 27 show variants of applicator members according to the invention in cross section, FIG. 28 illustrates a variant embodiment of the hinge.

The film deposited on the lips has the advantage of being very thin and of being virtually imperceptible to the user. It is thus a very light deposit that is deposited on the lips by means of the device which is the subject of the invention. This deposit is also non-tacky, and does not introduce a sensation of dryness. The deposit thus obtained does not migrate, does not transfer, and has a very good wear property.

It should be noted that, in the remainder of the description, unless otherwise indicated, the limits indicated for a range are included in that range.

The contents are indicated relative to the weight of the composition, in other words, relative to the weight of the total composition.

The expressions "at least one" and "several" are used without distinction.

Device

A subject of the invention, according to one of its aspects, is thus an applicator member for applying a cosmetic product to human keratin materials, in particular to the lips, comprising a partially flocked applicator head.

Preferably, the applicator head comprises at least one flocked distal end, in particular a flocked exterior surround, more particularly extending according to a flocked strip, for example generally O-shaped, V-shaped or U-shaped.

According to one advantageous embodiment, the applicator head has two opposite faces, the applicator head comprising:

a first part having at least one housing, and
a second part that is connected to the first part by a hinge and is at least partially engaged in the housing of the first part,
wherein the first and second parts are both accessible on each of said faces of the applicator head.

The applicator head can have a flattened overall shape and said faces can correspond to the main faces.

The invention affords new possibilities for producing the applicator member, with different surface states and/or different materials on the first and second parts. In particular, the invention makes it very easily possible for only one of the parts to be flocked, if so desired, or for them to be flocked differently. Such partial flocking, limited to one of the parts, also gives the applicator an attractive appearance.

The expression "are both accessible on each of said faces of the applicator head" is understood as meaning that, on each of these faces, the first and second parts are at least partially present at the surface and/or accessible through a through-opening. This can make it possible, if desired, to produce the applicator member such that, during the application of the cosmetic product from one of said faces, the human keratin materials come into contact with at least one of the first and second parts, better still into contact with both if the user so desires.

Along at least a portion of the length of the applicator member, it is possible for both portions to be visible on each of said faces; in a variant, along at least a portion of the length of the applicator member, only one of the parts is visible on one of said faces. The body of the applicator member can be produced in one piece, by moulding thermoplastic elastomer(s) (TPE).

"Thermoplastic elastomers" is generally intended to mean polymers or a blend of polymers that have, at the service temperature, properties similar to those of vulcanized rubber. These properties disappear at the processing temperature, making subsequent processing possible, but reappear when the material returns to the service temperature (cf. standard ISO 18064:2014).

For general information on thermoplastic elastomers, reference may in particular be made to the guide from *Techniques de l'Ingénieur* [*Techniques of the Engineer*], *Traité Plastiques et Composites* [*Treatise on Plastics and Composites*], *AM* 3 400 by Michel Biron published on 10 Jul. 2000.

From the chemical point of view, Hytrel® is an ether-ester copolymer (COPE) belonging to the family of thermoplastic elastomers (TPEs).

More specifically, Hytrel® is a block copolymer comprising hard (crystalline or semi-crystalline) segments of polybutylene terephthalate and soft (amorphous) segments of polyesters based on long-chain glycols.

The properties of Hytrel®, including the hardness which is often used for naming the grades, vary greatly as a function in particular of the ratio between the hard segments and soft segments, and of the chemical composition of these segments.

Preferably, the housing in the first part is a through-housing, thereby allowing access to the second part from each of said faces of the applicator head.

According to one particular embodiment of the invention, the user makes use of a reservoir of product and the applicator member belongs, for example, to an applicator designed to close this container when not in use.

Preferably, the abovementioned hinge is disposed on the applicator member away from the distal end of the applicator head. The hinge is preferably a film hinge or comprises two flexible strands. The hinge can be moulded with the body of the applicator member from a thermoplastic material.

At least one of the first and the second part, preferably the first part, is at least partially, better still entirely, flocked. The flocking bristles allow better retention of the cosmetic product on the applicator member and make it easier to spread it over the area to be treated. Preferably, the other of the first and the second part, in particular the second part, is non-flocked. This makes it possible, if desired, to limit the quantity of cosmetic product that collects on the applicator member.

This other part can be produced without a cavity forming a reservoir.

One or more reliefs can be produced on this other part in order to exert for example a massaging action on the skin or the lips.

In a variant, this other part is at least partially flocked, but the flocking of the first part can be different from the flocking of the second part, in particular in terms of quantity of fibres, sizes of fibres and/or physical properties of the fibres, for example stiffness of the fibres. Two different flockings can make it possible to have different effects during the application of the cosmetic product. In addition, attractive aesthetic effects can be obtained, by using for example different colours for the fibres.

At least one of the first and second parts, more particularly the second part, can have protruding or recessed reliefs, for example in the form of bosses, ridges or grooves, in particular in a regular arrangement.

The protruding reliefs can also be produced so as to make it possible to exert a massaging effect, in particular on the lips during the application of the cosmetic product. The recessed reliefs can promote the accumulation of product on the applicator member and enhance the autonomy thereof.

The second part may bear a pattern or an inscription in the form of a relief or impression.

Preferably, the first and second parts are free of such reliefs.

Preferably, the second part takes up all of the housing of the first part. The second part may be engaged entirely in the corresponding housing of the first part.

The first part may be produced with two arms that meet at their ends and define between one another the housing in which the second part is engaged.

When one of said faces is viewed from the front, the first part can extend all around the second part. The first part can bear a flocked coating all around the second part.

The applicator head can have a width which decreases, in front view, in the direction of its free end.

The two arms of the second part can converge towards one another in the direction of the distal free edge.

The applicator head can have, in side view, a thickness which varies relatively little in the direction of the distal free edge, in particular which varies by less than 25% from a thickness at a given location, along 90% of its length. The expression "side view" denotes a view perpendicularly to a median plane for said faces, this median plane being substantially perpendicular to the flattening plane of the applicator head.

The contour of the second part may be rounded both in cross section and when it is viewed from the front.

Preferably, the first part is made of a flexible material, in particular elastomer.

The first and the second part preferably form a single part moulded in a thermoplastic material.

Preferably, the applicator head is attached to a mounting or gripping end piece of the applicator member. The end piece is preferably formed from two half end pieces that are connected together by the abovementioned hinge. Preferably, this hinge is disposed at the end of the end piece away from the applicator head. The two half end pieces can be flapped together to form the complete end piece, serving for example to be mounted in an applicator stem.

The applicator member may comprise an end piece substantially in the form of a cylinder of revolution, formed by two half end pieces; each half end piece can be attached to one of said parts by a flared transition zone that widens in the direction of the corresponding part.

A portion of the applicator member can be overmoulded on the rest of the applicator, in particular in a different material.

The applicator head can extend with its longitudinal axis aligned with that of the end piece. In a variant, the longitudinal axis of the applicator head forms a non-zero angle with that of the end piece.

The first and the second part can be fixed together in the use configuration, so as to be easily disassemblable or not, by snap-fastening or force-fitting. The second part may comprise a protruding relief at its periphery, said protruding relief cooperating with a recessed relief on the first part, or vice versa. In a variant, the two half end pieces or the first and second parts comprise other cooperating reliefs that make it possible to keep the first and second parts in the use configuration.

The first part may comprise a fixing hook and/or the second part may comprise a fixing tab, the fixing hook being inserted into or under the through-opening in the second part and the fixing tab engaging in the housing of the first part, the fixing tab cooperating with the fixing hook in order to keep the second part folded over the first part. Preferably, the fixing tab has a tooth which, during the folding of the second part over the first part, engages with the fixing hook by snap-fastening.

Preferably, one of the fixing hook and the fixing tab, in particular the fixing tab, is flush with the surface of one of the main faces.

In a further variant, the first and the second part are not fixed together but only folded together. The first and second parts are then held for example by the introduction of the end piece of the applicator member into a recess in a stem, the end piece fitting for example tightly in this recess or the stem being crimped on the end piece, such that the two half end pieces, and as a result the first and the second part, are kept pressed together.

A further subject of the invention, according to another of its aspects, is a device for applying a product to human keratin materials, comprising:
  a stem,
  an applicator member according to the invention, according to the first or the second aspect as defined above, the applicator member being fixed to the end of the stem.

The end piece of the applicator member is preferably inserted into an open recess at the end of the stem.

Preferably, the device comprises a container containing the cosmetic product to be applied. This container may comprise a wiping member.

The device can serve for the application of the product to keratin materials, in particular to the lips.

The container contains the composition that will be described below.

A further subject of the invention, according to another of its aspects, is a method for manufacturing an applicator member according to the invention, comprising the steps consisting in:
  moulding a body of the applicator member in the open state, comprising
    a first part having at least one housing, and
    a second part that is connected to the first part by a hinge and is intended to be engaged in the housing after the second part has been folded over the first part,
  applying an adhesive to one of the first and the second part, preferably to the first part,
  applying flocking bristles to the adhesive,
  folding the second part over the first part so that the second part is at least partially engaged in the housing of the first part.

Preferably, the body of the applicator member comprises two half end pieces that are attached at their distal ends to the first and the second part, respectively, and are connected together at their proximal ends by the hinge.

The second part can be fixed to the first part by snap-fastening or force-fitting. In a variant, the second part and the first part are only folded together and kept in this state by an additional means, for example a stem into which the end piece is inserted.

A further subject of the invention is a method for manufacturing a device according to the invention, comprising the step consisting in fixing the applicator member as defined above to a stem, for example by insertion of the end piece into an open housing at the end of the stem.

The invention may be better understood from reading the following detailed description of non limiting exemplary embodiments thereof and from examining the appended drawing, in which:— FIG. 1 shows an example of a packaging and application device according to the invention, FIG. 2 schematically illustrates an example of an applicator member according to the invention, FIG. 3 shows a front view of the applicator member from FIG. 2, along III in FIG. 2, FIG. 4 shows a side view of the applicator member from FIGS. 2 and 3, along IV in FIG. 2, FIG. 5 shows the body of the applicator member from FIG. 2 in the open configuration, FIG. 6 illustrates a top view of the body of the applicator member from FIG. 5, along VI in FIG. 5, FIG. 7 shows a side view of the body of the applicator member from FIGS. 5 and 6, along VII in FIG. 6, FIG. 8 is a cross section on VIII-VIII in FIG. 6, FIG. 9 is a cross section on IX-IX in FIG. 6, FIG. 10 is a cross section on X-X in FIG. 3, FIG. 11 schematically illustrates a variant embodiment of the body of the applicator member, in the open configuration, FIG. 12 schematically and partially shows a front view of the applicator member from FIG. 11, following assembly, FIGS. 13 to 20 are schematic perspective views of variant embodiments of applicator members according to the invention, FIG. 21 shows a front view of another variant of an applicator member, FIGS. 22 to 23 show variants of applicator members according to the invention in cross section, The packaging and application device 1 illustrated in FIG. 1 comprises a container 10 containing a product P to be applied and an applicator 3 for taking up and applying the product contained in the container.

The applicator 3 comprises a stem 4 of longitudinal axis X, bearing at one 5 of its ends an applicator member 8 comprising an applicator head 9. As can be seen in FIGS. 2 to 4, the applicator head 9 comprises a first part 15 and a second part 17 that is engaged in the first part 15, these two parts being connected together by a hinge 34.

In the example illustrated, the axis X of the stem 4 is rectilinear, but it could be curved in a variant.

The container 10 may comprise in its upper part a neck 21, as illustrated. A wiping member 24 is engaged in this neck 21.

As illustrated in FIG. 1, the stem 4 is provided at its other end 6 with a gripping element 13 that also forms a cap for leaktight closure of the container 10.

The distal end 5 of the stem 4 has a recess which receives a mounting end piece 30 of the applicator member 8.

The applicator head 9 extends along a longitudinal axis T and is attached to the end piece 30. The latter is formed by two half end pieces 30a and 30b that are in contact with one another and connected together by the hinge 34.

The two half end pieces 30a and 30b are connected to the first part 15 and to the second part 17, respectively. The end piece 30 can be held in the stem 4 by any means, in particular by adhesive bonding, force-fitting, stapling, screw-fastening, crimping or snap-fastening.

Preferably, the two half end pieces 30a and 30b each have a flat face 31a and 31b, the latter coming into contact with one another over their entire surface area. In a variant, these faces comprise one or more reliefs that cooperate, for example by snap-fastening.

Thus, the possibility for one of the half end pieces 30a or 30b to comprise a recessed relief 75 for receiving the other half end piece has been illustrated in FIG. 11.

Preferably, the end piece 30 is in the form of a cylinder of revolution in the case of mounting in a stem. The end piece can be realized in a different manner, in particular when it is intended to serve directly for gripping.

Preferably, the hinge 34 is disposed at those ends 36a and 36b of the two half end pieces 30a and 30b that are away from the first and second parts 15 and 17. It allows the two parts 15 and 17 and the two half end pieces 30a and 30b to be moulded in the open configuration in one piece and to be assembled by the second part 17 and the half end piece 30b being rotated about an axis Y of the hinge 34, perpendicular to the longitudinal axis Z of the end piece 30, as illustrated in FIGS. 5 to 7.

The applicator head 9 can be flattened overall in a plane M perpendicular to the plane of FIG. 4 and defines two opposite main faces 18 and 19. Preferably, the applicator head 9 has a greater width L which is greater than that D of the end piece 30.

The first part 15 can be flocked, as illustrated in FIG. 1, and the second part 17 can comprise reliefs such as a plurality of ribs 27, as illustrated in FIG. 2. The ribs 27 extend preferably obliquely relative to the longitudinal axis T, forming an angle β with the longitudinal axis T.

The longitudinal axis T of the applicator head 9 preferably forms an angle α of preferably less than 45°, better still between 10 and 45°, with the longitudinal axis Z of the end piece 30.

As illustrated in FIGS. 5 to 7, the first and second parts 15 and 17 can each be attached to a respective half end piece 30a or 30b by way of a corresponding intermediate portion 43a or 43b which widens in the direction of the associated part. Preferably, the intermediate portions 43a and 43b are symmetrical such that when they are folded one over the other, the applicator member 8 has no discontinuities in its portion extending between the end piece 30 and the applicator head 9.

The hinge 34 is preferably a film hinge, as illustrated in FIGS. 5 to 7.

In the example in question, the first part 15 comprises two arms 48 that meet at their ends and define between one another a housing 40, in particular a through-housing, for receiving the second part 17. Preferably the first part 15 surrounds the second part 17 when the applicator member is viewed from the front, as in FIG. 3.

The housing 40 and the second part 17 have for example an approximately oval contour, as illustrated.

The second part 17 may entirely fill the housing 40.

The applicator head 9 can narrow slightly towards its free end, as illustrated in FIGS. 4 and 7.

As can be seen in particular in FIGS. 8 and 9, the first and second parts 15 and 17 can have respective thicknesses $e_a$ and $e_b$ which are greater than those $d_a$ and $d_b$ of the intermediate parts 43a and 43b.

The total thickness e of the applicator head can be less than its greatest width L, as can be seen in FIG. 10.

As illustrated in FIG. 8, the second part 17 can have an approximately rectangular cross section and comprise a rib 50 at its periphery 47.

It can be seen in FIG. 9 that each arm 48 of the first part 15 can comprise a corresponding groove 53.

As illustrated in FIG. 10, the rib 50 is snap-fastened, during the folding of the second part 17 over the first part 15, into the groove 53 in order to keep the applicator member 8 in the closed position.

This does not have to be the case, and in particular the first part 15 can comprise a rib that is snap-fastened into a groove in the second part 17, or the first and the second part 15 and 17 do not have any relief for snap-fastening.

FIGS. 11 and 12 show a variant embodiment which differs from the example in FIGS. 1 to 10 by the shape of the second part 17.

The latter comprises a cavity 70, which is not a through-cavity, containing the cosmetic product P, which is thus only accessible from one side of the applicator member.

The cosmetic composition P will be described below.

One of the half end pieces 30a and 30b can be wider than the other. For example, a recessed relief 75 extends along the half end piece 30a in order to receive the half end piece 30b.

Figures 13, 14, 15, 16:
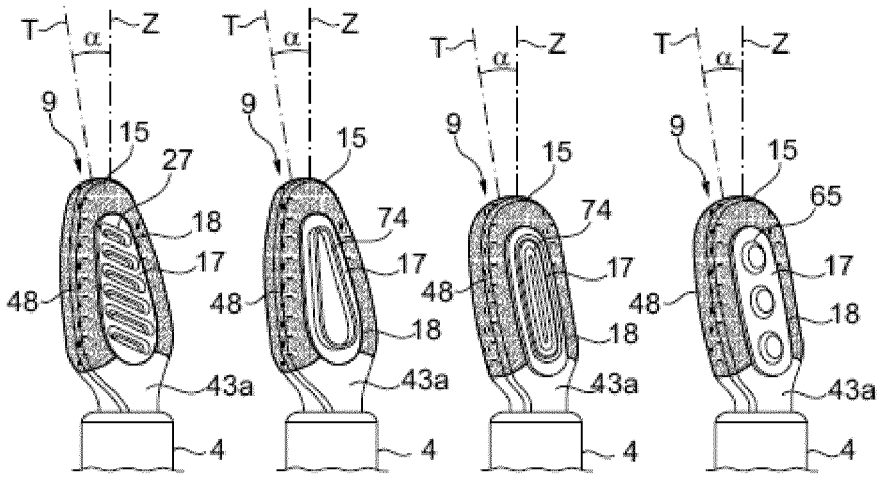
Figures 17, 18, 19, 20:
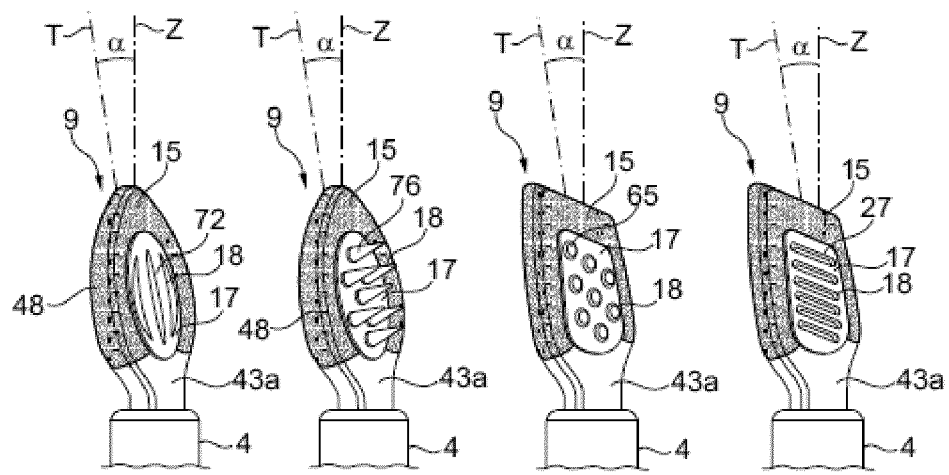

In the variants illustrated in FIGS. 13 to 20, the second part 17 comprises protruding or recessed reliefs of different shapes, in particular bosses 65, as illustrated in FIGS. 16, 18 and 19, oblique or transverse ridges 27, as illustrated in FIGS. 13 and 20, longitudinal grooves 72, as illustrated in FIG. 17, cavities 74, as illustrated in FIGS. 14 and 15, or spikes 76, as illustrated in FIG. 18.

When viewed from the front, the contour of the applicator head, along a major part of the length which is flocked, may be approximately elliptical, as illustrated in FIGS. 17 and 18, rectangular, as illustrated in FIGS. 19 and 20, have parallel side edges connected by a rounding, as in FIGS. 15 and 16, or have outwardly convex edges connected by a rounding, as in FIGS. 13 and 14.

In the variant illustrated in FIG. 21, the second part 17 bears a relief 80 or an impression representing for example a decorative logo or an inscription that helps the user to get his/her bearings during use.

In the example in this figure, the end piece serves to be gripped directly by the user.

The end piece 30 can still be inserted into a covering element that serves as a gripping member.

FIGS. 22 to 27 show various examples of arrangements of the first 15 and second 17 parts of the applicator head in cross section.

In the example of FIG. 22, the applicator head has a general shape that is flattened along a flattening plane M. The second part 17 has for example as illustrated a cross section in the overall shape of an hourglass, which is held by complementing shapes in the housing 40 of the first part 15. The applicator part may have a symmetrical shape with respect to a plane of symmetry S which may be perpendicular to the flattening plane M.

In the example in FIG. 23, the applicator head has the overall shape of an almond in cross section. The extents taken up by the second part on each of the opposite faces 18 and 19 of the applicator head may be different. In the example illustrated, the second part 17 thus takes up a smaller portion of the face 18 than of the face 19, the part 17 being wider at its base. The portion of the application surface that is defined by the second part 17 may have a smaller radius of curvature on the side of the face 18 than on the side of the face 19. In FIG. 37, the applicator head has a symmetrical shape with respect to the plane of symmetry S, but, in a variant that is not illustrated, the applicator head has an asymmetrical shape with respect to a median plane that intersects it half-way along its length.

As in the example in FIG. 22, the second part has a narrowing of its section between the faces 18 and 19, this keeping the second part in place in the housing 40. The plane in which the second part becomes narrowest may coincide, as illustrated, with the plane in which the first part 15 is at its widest. In the example in FIG. 23, the applicator head has a section which is asymmetrical with respect to a plane that intersects it half-way through its thickness.

In the example in FIG. 24, the applicator head has a cross section which has an oval, for example elliptical, overall shape. The major axis of the section may be contained in a median plane M that intersects the applicator head half-way through its thickness. The applicator head may have a symmetrical overall shape with respect to a plane of symmetry S perpendicular to the median plane M.

The examples in FIGS. 25 to 27 differ from those in FIGS. 22 to 24 by the presence of flocked coatings 215 and 218 on the first 15 and second parts 17.

In the examples illustrated, the flocked coating 218 of the second part 17 does not extend over the surfaces thereof that face the first part 15, in the housing 40. In a variant that is not illustrated, the coating 218 runs onto these surfaces and the assembly of the first and second parts makes it possible to hide the flocked coating that runs onto said surfaces, thereby making it possible to obtain clean contours on each of the faces 18 and 19.

The same may go for the flocked coating 215 which extends over the first part. This coating can run into the housing 40 and be partially hidden by the second part when the latter is placed in position.

The flocked coatings 215 and 218 of the first 15 and second 17 parts are for example made of flock fibres which differ in terms of their length and/or their diameter, the material used and/or their colour.

The hinge can be realized as illustrated in FIG. 28, with two flexible strands 234 which are attached to each of the parts 15 and 17 at a distance from their proximal end. The strands form a sort of frame in top view, in the moulding configuration.

The invention is not limited to the examples illustrated.

In particular the features of the various examples illustrated can be combined as parts of variants which are not illustrated.

For example, in a general manner, the two parts can be flocked, the flockings being different; one of the parts may comprise a relief of a certain type on one side and a different type of relief on the other side so as to have different effects on one side of the applicator and the other.

Composition

As indicated previously, the composition, particularly used in the device that has just been described, is in the form of an emulsion.

The composition is advantageously in the form of a liquid emulsion.

The term "liquid" is intended to mean a fluid texture, the viscosity of which at 25° C. is more particularly between 0.005 and 12 Pa·s, preferably between 0.01 and 10 Pa·s and even more advantageously between 0.05 and 8 Pa·s.

Preferably, the viscosity at 25° C. of a composition according to the invention is between 0.1 and 6 Pa·s.

Protocol for Measuring the Viscosity:

The viscosity measurement is generally performed at 25° C., using a Rheomat RM180 viscometer equipped with a No. 2 or 3 spindle, the measurement being performed after 10 minutes of rotation of the spindle in the formula, at a shear rate of 200 revolutions/min (rpm).

The composition may be in the form of a direct (oil-in-water) or inverse (water-in-oil) emulsion.

According to one preferred embodiment of the invention, the composition is in the form of an inverse (water-in-oil) emulsion.

Moreover, the composition according to the invention comprises, in addition to the water, at least one particular film-forming polymer and at least non-volatile oils, one of which is chosen from polar hydrocarbon-based non-volatile oils, the other of which is chosen from phenyl silicone non-volatile oils, preferably free of dimethicone fragment.

The composition according to the invention could also comprise other additional non-polar hydrocarbon-based or non-phenyl silicone non-volatile oils.

The total content of non-volatile oils preferably represents from 6 to 20% by weight, and in accordance with an even more particular embodiment, from 6 to 15% by weight, relative to the weight of the composition.

Polar Non-Volatile Hydrocarbon-Based Oils

As previously indicated, the composition used in the device in accordance with the invention comprises at least one polar non-volatile hydrocarbon-based oil.

The term "oil" is intended to mean a water-immiscible non-aqueous compound which is liquid at 25° C. and atmospheric pressure ($1.013 \times 10^5$ Pa).

The term "immiscible" is intended to mean that the mixing of the same amount of water and oil, after stirring, does not result in a stable solution comprising only a single phase, under the above-mentioned temperature and pressure conditions. Observation is carried out by eye or using a phase contrast microscope, if necessary, on 100 g of mixture obtained after sufficient Rayneri stirring to produce a vortex within the mixture (by way of indication, 200 to 1000 rev/min), the resulting mixture being left standing, in a closed flask, for 24 hours at ambient temperature before observation.

The term "non-volatile oil" is intended to mean an oil of which the vapour pressure at 25° C. and atmospheric pressure is non-zero and is less than $10^{-3}$ mmHg (0.13 Pa).

The term "hydrocarbon-based oil" is intended to mean an oil formed essentially from, or even constituted of, carbon and hydrogen atoms, and optionally oxygen and nitrogen atoms, and not containing any silicon or fluorine atoms.

It can contain alcohol, ester, ether, carboxylic acid, amine and/or amide groups.

Preferably, the hydrocarbon-based oil is, in addition to being free of silicon and fluorine, free of heteroatoms such as nitrogen, sulfur and phosphorus. The hydrocarbon-based oil is thus distinct from a silicone oil and a fluorinated oil.

In the present case, the polar non-volatile hydrocarbon-based oil comprises at least one oxygen atom.

In particular, this non-volatile hydrocarbon-based oil comprises at least one alcohol function (it is then an "alcohol oil") and/or at least one ester function (it is then an "ester oil").

The ester oils that may be used in the compositions according to the invention may in particular be hydroxylated.

The composition according to the invention may comprise one or more non-volatile hydrocarbon-based oils, in particular chosen from:

$C_{10}$-$C_{26}$ alcohols, preferably monoalcohols;

More particularly, the $C_{10}$-$C_{26}$ alcohols are saturated or unsaturated and branched or unbranched and comprise from 10 to 26 carbon atoms.

Preferably, the $C_{10}$-$C_{26}$ alcohols are fatty alcohols, which are preferably branched when they comprise at least 16 carbon atoms.

As examples of fatty alcohols that may be used according to the invention, mention may be made of linear or branched fatty alcohols, of synthetic origin or alternatively of natural origin, for instance alcohols derived from plant materials (coconut, palm kernel, palm, etc.) or animal materials (tallow, etc.).

Needless to say, other long-chain alcohols may also be used, for instance ether alcohols or alternatively "Guerbet" alcohols.

Finally, use may also be made of certain fractions of alcohols of varying length of natural origin, for instance coconut ($C_{12}$ to $C_{16}$) or tallow ($C_{16}$ to $C_{18}$) or compounds of diol or cholesterol type.

Preferably, a fatty alcohol comprising from 10 to 24 carbon atoms is used.

Mention may in particular be made, as specific examples of fatty alcohols which can preferably be used, of lauryl alcohol, isostearyl alcohol, oleyl alcohol, 2-butyloctanol, 2-undecylpentadecanol, 2-hexyldecyl alcohol, isocetyl alcohol, octyldodecanol and mixtures thereof.

optionally hydroxylated monoesters, diesters or triesters of a $C_2$-$C_8$ monocarboxylic or polycarboxylic acid and of a $C_2$-$C_8$ alcohol.
  In particular:
  optionally hydroxylated monoesters of a $C_2$-$C_8$ carboxylic acid and of a $C_2$-$C_8$ alcohol,
  optionally hydroxylated diesters of a $C_2$-$C_8$ dicarboxylic acid and of a $C_2$-$C_8$ alcohol, such as diisopropyl adipate, 2-diethylhexyl adipate, dibutyl adipate, diisostearyl adipate or 2-diethylhexyl succinate,
  optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate;
  esters of a $C_2$-$C_8$ polyol and of one or more $C_2$-$C_8$ carboxylic acids, such as glycol diesters of monoacids, such as neopentyl glycol diheptanoate, or glycol triesters of monoacids, such as triacetin.
  ester oils, in particular having between 18 and 70 carbon atoms.

Examples that may be mentioned include monoesters, diesters or triesters.

The ester oils may be hydroxylated or non-hydroxylated.

The non-volatile ester oil may for example be chosen from:

monoesters comprising between 18 and 40 carbon atoms in total, in particular the monoesters of formula $R_1COOR_2$ in which $R_1$ represents a saturated or unsaturated, linear or branched or aromatic fatty acid residue comprising from 4 to 40 carbon atoms and $R_2$ represents a hydrocarbon-based chain, which is in particular branched, containing from 4 to 40 carbon atoms, on condition that $R_1+R_2 \geq 18$, for instance Purcellin oil (cetostearyl octanoate), isononyl isononanoate, $C_{12}$ to $C_{15}$ alkyl benzoate, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate or 2-octyldodecyl myristate.

Preferably, they are esters of formula $R_1COOR_2$ in which $R_1$ represents a linear or branched fatty acid residue containing from 4 to 40 carbon atoms and $R_2$ represents a hydrocarbon-based chain that is in particular branched, containing from 4 to 40 carbon atoms, $R_1$ and $R_2$ being such that $R_1+R_2 \geq 18$.

Even more particularly, the ester comprises between 18 and 40 carbon atoms in total.

Preferred monoesters that may be mentioned include isononyl isononanoate, oleyl erucate and/or 2-octyldodecyl neopentanoate;

monoesters of a fatty acid, in particular of 18 to 22 carbon atoms, and in particular of lanolic acid, oleic acid, lauric acid or stearic acid, and of diols, for instance propylene glycol monoisostearate;
  diesters, in particular comprising between 18 and 60 carbon atoms in total and in particular between 18 and 50 carbon atoms in total. Use may be made especially of diesters of a dicarboxylic acid and of monoalcohols, preferably such as diisostearyl malate, or glycol diesters of monocarboxylic acids, such as neopentyl glycol diheptanoate, propylene glycol dioctanoate, diethylene glycol diisononanoate or polyglyceryl-2 diisostearate (in particular such as the compound sold under the commercial reference Dermol DGDIS by the company Alzo);
  hydroxylated monoesters and diesters, preferably with a total carbon number ranging from 18 to 70, for instance polyglyceryl-3 diisostearate, isostearyl lactate, octyl hydroxystearate, octyldodecyl hydroxystearate, diisostearyl malate or glyceryl stearate;
  triesters, in particular comprising between 35 and 70 carbon atoms in total, in particular such as triesters of a tricarboxylic acid, such as triisostearyl citrate, or tridecyl trimellitate, or glycol triesters of monocarboxylic acids such as polyglyceryl-2 triisostearate;
  tetraesters, in particular with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, polyglyceryl-2 tetraisostearate or pentaerythrityl tetrakis(2-decyl) tetradecanoate;

polyesters obtained by condensation of an unsaturated fatty acid dimer and/or trimer and of diol, such as those described in patent application FR 0 853 634, in particular such as dilinoleic acid and 1,4-butanediol. Mention may in particular be made on this account of the polymer sold by Biosynthis under the name Viscoplast 14436H (INCI name: dilinoleic acid/butanediol copolymer) or else copolymers of polyols and of diacid dimers, and their esters, such as Hailucent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{34}$, especially of $C_{12}$ to $C_{22}$, in particular of $C_{18}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

polyesters resulting from the esterification of at least one triglyceride of hydroxylated carboxylic acid(s) with an aliphatic monocarboxylic acid and with an aliphatic dicarboxylic acid, which is optionally unsaturated, for instance the succinic acid and isostearic acid castor oil sold under the reference Zenigloss by Zenitech;

hydrocarbon-based plant oils such as fatty acid triglycerides (which are liquid at ambient temperature), especially of fatty acids containing from 7 to 40 carbon atoms, such as heptanoic or octanoic acid triglycerides or jojoba oil; mention may be made in particular of saturated triglycerides such as caprylic/capric triglyceride and mixtures thereof, for example such as the product sold under the reference Myritol 318 from Cognis, glyceryl triheptanoate, glyceryl trioctanoate, and $C_{18-36}$ acid triglycerides such as those sold under the reference Dub TGI 24 by Stéarineries Dubois, and unsaturated triglycerides such as castor oil, olive oil, ximenia oil and pracaxi oil;

vinylpyrrolidone/1-hexadecene copolymers, for instance the product sold under the name Antaron V-216 (also known as Ganex V216) by the company ISP (MW=7300 g/mol).

$C_{12}$-$C_{26}$ fatty acids, preferably $C_{12}$-$C_{22}$ fatty acids, which are preferably unsaturated, such as oleic acid, linoleic acid or linolenic acid, and mixtures thereof.

dialkyl carbonates, the 2 alkyl chains possibly being identical or different, such as dicaprylyl carbonate sold under the name Cetiol CC® by Cognis.

and mixtures thereof.

At least one fatty alcohol comprising from 20 to 26 carbon atoms, and most particularly octyldodecanol is preferably used as polar non-volatile hydrocarbon-based oil.

Preferably, the content of non-volatile polar hydrocarbon-based oil(s) is between 5% and 15% by weight and preferably from 6% to 12% by weight relative to the weight of the composition.

Non-Volatile Phenyl Silicone Oils

The composition used in the device in accordance with the invention also comprises at least one non-volatile phenyl silicone oil, preferably without dimethicone fragment.

The term "silicone oil" is intended to mean an oil containing at least one silicon atom and in particular containing Si—O groups.

The expression "phenyl silicone oil" denotes a silicone oil bearing at least one phenyl substituent.

It should be noted that the term "dimethicone fragment" denotes a divalent siloxane group in which the silicon atom bears two methyl radicals, this group not being located at the ends of the molecule. It can be represented by the following formula: —(Si(CH$_3$)$_2$—O)—.

The silicone oils generally have a molecular weight of less than or equal to 150 000 g/mol, preferably less than or equal to 100 000 g/mol and better still less than or equal to 10 000 g/mol. The weight-average molecular weights are measured in a manner that is conventional in the field, for example using gel permeation chromatography coupled to static light scattering (GPC-MALLS).

The non-volatile phenyl silicone oil may thus be chosen from:

phenyl silicone oils optionally having a dimethicone fragment corresponding to formula (I) below:

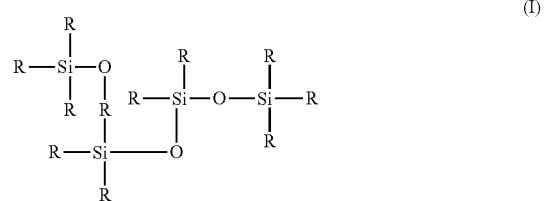

in which the groups R, which are monovalent or divalent, represent, independently of each other, a methyl, methylene, phenyl or phenylene, with the proviso that at least one group R represents a phenyl.

Preferably, in this formula, the phenyl silicone oil comprises at least three phenyl groups, for example at least four, at least five or at least six.

phenyl silicone oils optionally having a dimethicone fragment corresponding to formula (II) below:

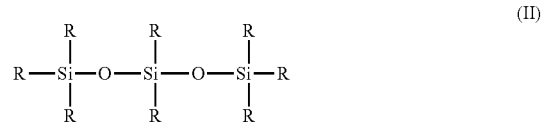

in which the groups R represent, independently of each other, a methyl or a phenyl, with the proviso that at least one group R represents a phenyl.

Preferably, in this formula, the compound of formula (II) comprises at least three phenyl groups, for example at least four or at least five.

Mixtures of different phenylorganopolysiloxane compounds described above can be used.

Examples which may be mentioned comprise mixtures of triphenyl-, tetraphenyl- or pentaphenylorganopolysiloxanes.

Mention may more particularly be made, among the compounds of formula (II), of phenyl silicone oils not having a dimethicone fragment, corresponding to the formula (II) in which at least 4 or at least 5 R radicals represent a phenyl radical, the remaining radicals representing methyls.

Such non-volatile phenyl silicone oils are preferably trimethylpentaphenyltrisiloxane or tetramethyltetraphenyltrisiloxane. They are in particular sold by Dow Corning under the reference PH-1555 HRI or Dow Corning 555 Cosmetic Fluid (chemical name: 1,3,5-trimethyl-1,1,3,5,5- pentaphenyltrisiloxane; INCI name: trimethylpentaphenyl-trisiloxane), or the tetramethyltetraphenyltrisiloxane sold under the reference Dow Corning 554 Cosmetic Fluid by Dow Corning can also be used.

They correspond in particular to formulae (III) and (III') below:

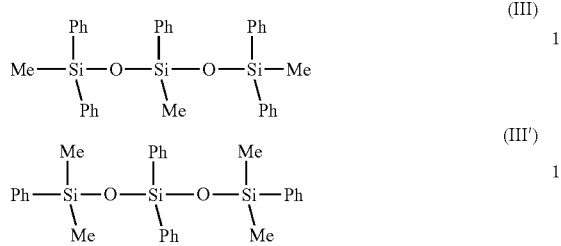

in which Me represents methyl, and Ph represents phenyl.
phenyl silicone oils having at least one dimethicone fragment corresponding to formula (IV) below:

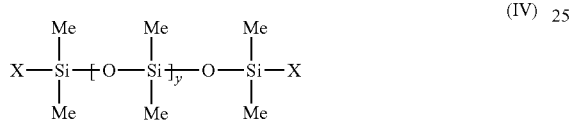

in which Me represents methyl, y is between 1 and 1000 and X represents —CH$_2$—CH(CH$_3$)(Ph).

phenyl silicone oils corresponding to formula (V) below, and mixtures thereof:

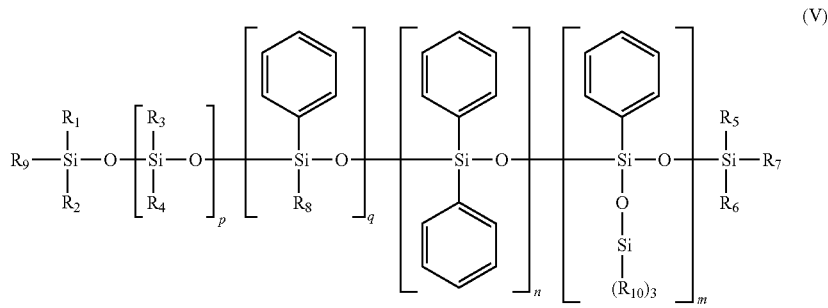

in which:
R$_1$ to R$_{10}$, independently of one another, are saturated or unsaturated and linear, cyclic or branched C$_1$-C$_{30}$ hydrocarbon-based radicals, m, n, p and q are, independently of each other, integers between 0 and 900, with the proviso that the sum m+n+q is other than 0.

Preferably, the sum m+n+q is between 1 and 100. Advantageously, the sum m+n+p+q is between 1 and 900 and preferably between 1 and 800.

Preferably, q is equal to 0.

More particularly, R$_1$ to R$_{10}$ represent, independently of one another, a saturated or unsaturated, preferably saturated, and linear or branched C$_1$-C$_{30}$ hydrocarbon-based radical, and in particular a preferably saturated C$_1$-C$_{20}$, in particular C$_1$-C$_{18}$, hydrocarbon-based radical, or a monocyclic or polycyclic C$_6$-C$_{14}$ and in particular C$_{10}$-C$_{13}$ aryl radical, or an aralkyl radical, the alkyl part of which is preferably a C$_1$-C$_3$ alkyl part.

Preferably, R$_1$ to R$_{10}$ can each represent a methyl, ethyl, propyl, butyl, isopropyl, decyl, dodecyl or octadecyl radical, or in an alternative form a phenyl, tolyl, benzyl or phenethyl radical. R$_1$ to R$_{10}$ can in particular be identical, and in addition can be a methyl radical.

As particular embodiments of formula (V), mention may be made of:
phenyl silicone oils optionally having at least one dimethicone fragment corresponding to formula (VI) below, and mixtures thereof:

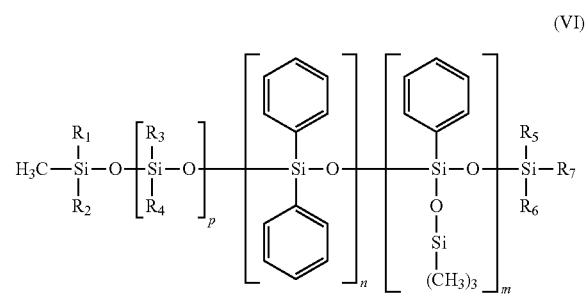

in which:
R$_1$ to R$_6$, independently of each other, are saturated or unsaturated, linear, cyclic or branched C$_1$-C$_{30}$ hydrocarbon-based radicals, a preferably C$_6$-C$_{14}$ aryl radical or an aralkyl radical, the alkyl part of which is C$_1$-C$_3$ alkyl,

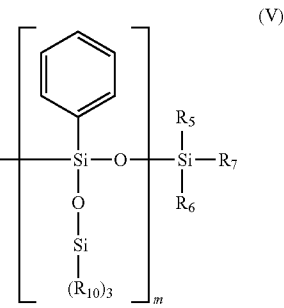

m, n and p are, independently of each other, integers between 0 and 100, with the proviso that the sum n+m is between 1 and 100.

Preferably, R$_1$ to R$_6$ represent, independently of one another, a C$_1$-C$_{20}$, in particular C$_1$-C$_{18}$, hydrocarbon-based, preferably alkyl, radical, or a C$_6$-C$_{14}$ aryl radical which is monocyclic (preferably a C$_6$ aryl radical) or polycyclic and in particular a C$_{10}$-C$_{13}$ aryl radical, or an aralkyl radical (preferably the aryl part is a C$_6$ aryl part; the alkyl part is a C$_1$-C$_3$ alkyl part).

Preferably, R$_1$ to R$_6$ can each represent a methyl, ethyl, propyl, butyl, isopropyl, decyl, dodecyl or octadecyl radical, or in an alternative form a phenyl, tolyl, benzyl or phenethyl radical.

R$_1$ to R$_6$ can in particular be identical, and in addition can be a methyl radical. Preferably, m=1 or 2 or 3, and/or n=0 and/or p=0 or 1 may be applied, in formula (VI).

According to a particular embodiment, the non-volatile phenyl silicone oil is chosen from phenyl silicone oils bearing at least one dimethicone fragment.

Preferably, such oils correspond to compounds of formula (VI) in which:
m=0 and n and p are, independently of each other, integers between 1 and 100.

Preferably, $R_1$ to $R_6$ are methyl radicals.

According to this embodiment, the silicone oil is preferably chosen from a diphenyl dimethicone, such as KF-54 from Shin-Etsu (400 cSt), KF54HV from Shin-Etsu (5000 cSt), KF-50-300CS from Shin-Etsu (300 cSt), KF-53 from Shin-Etsu (175 cSt) or KF-50-100CS from Shin-Etsu (100 cSt).
p is between 1 and 100, the sum n+m is between 1 and 100, and n=0.

These phenyl silicone oils optionally have at least one dimethicone fragment corresponding more particularly to formula (VII) below:

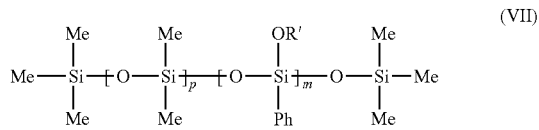

in which Me is methyl and Ph is phenyl, OR' represents an —OSiMe₃ group and p is 0 or is between 1 and 1000, and m is between 1 and 1000. In particular, m and p are such that compound (VII) is a non-volatile oil.

According to a first embodiment of non-volatile phenyl silicone having at least one dimethicone fragment, p is between 1 and 1000 and m is more particularly such that the compound (VII) is a non-volatile oil. Use may be made, for example, of trimethylsiloxyphenyl dimethicone, sold in particular under the reference Belsil PDM 1000 by Wacker.

According to a second embodiment of non-volatile phenyl silicone not having a dimethicone fragment, p is equal to 0 and m is between 1 and 1000, and in particular is such that the compound (VII) is a non-volatile oil.

Phenyltrimethylsiloxytrisiloxane, sold in particular under the reference Dow Corning 556 Cosmetic Grade Fluid (DC556), can be used, for example.

non-volatile phenyl silicone oils not having a dimethicone fragment corresponding to formula (VIII) below, and mixtures thereof:

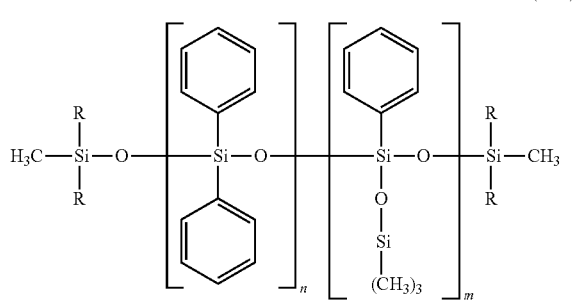

in which:
R, independently of each other, are saturated or unsaturated, linear, cyclic or branched $C_1$-$C_{30}$ hydrocarbon-based radicals, preferably R is a $C_1$-$C_{30}$ alkyl radical, a preferably $C_6$-$C_{14}$ aryl radical, or an aralkyl radical, the alkyl part of which is $C_1$-$C_3$ alkyl,
m and n are, independently of each other, integers between 0 and 100, with the proviso that the sum n+m is between 1 and 100.

Preferably, R, independently of each other, represent a saturated or unsaturated, preferably saturated, linear or branched $C_1$-$C_{30}$ hydrocarbon-based radical, and in particular a preferably saturated, $C_1$-$C_{20}$, in particular $C_1$-$C_{18}$ and more particularly $C_4$-$C_{10}$, hydrocarbon-based radical, a monocyclic or polycyclic $C_6$-$C_{14}$, and in particular $C_{10}$-$C_{13}$, aryl radical, or an aralkyl radical of which preferably the aryl part is $C_6$ aryl and the alkyl part is $C_1$-$C_3$ alkyl.

Preferably, the R groups can each represent a methyl, ethyl, propyl, butyl, isopropyl, decyl, dodecyl or octadecyl radical, or in an alternative form a phenyl, tolyl, benzyl or phenethyl radical.

The R groups can in particular be identical, and in addition can be a methyl radical.

Preferably, m=1 or 2 or 3, and/or n=0 and/or p=0 or 1 may be applied, in formula (VIII).

According to one preferred embodiment, n is an integer between 0 and 100 and m is an integer between 1 and 100, with the proviso that the sum n+m is between 1 and 100, in formula (VIII). Preferably, R is a methyl radical.

According to one embodiment, a phenyl silicone oil of formula (VIII) with a viscosity at 25° C. of between 5 and 1500 mm²/s (i.e. 5 to 1500 cSt), and preferably with a viscosity of between 5 and 1000 mm²/s (i.e. 5 to 1000 cSt), may be used.

According to this embodiment, the non-volatile phenyl silicone oil is preferably chosen from phenyl trimethicones (when n=0) such as DC556 from Dow Corning (22.5 cSt), or else from diphenylsiloxyphenyl trimethicone oil (when m and n are between 1 and 100) such as KF56 A from Shin-Etsu, or the Silbione 70663V30 oil from Rhone-Poulenc (28 cSt). The values in brackets represent the viscosities at 25° C.

phenyl silicone oils optionally having at least one dimethicone fragment corresponding to the following formula, and mixtures thereof:

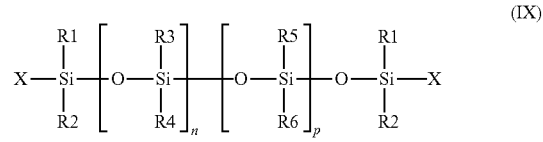

in which:
$R_1$, $R_2$, $R_5$ and $R_6$, which are identical or different, are an alkyl radical containing from 1 to 6 carbon atoms,
$R_3$ and $R_4$, which are identical or different, are an alkyl radical containing from 1 to 6 carbon atoms or an aryl radical (preferably a $C_6$-$C_{14}$ aryl radical), with the proviso that at least one of $R_3$ and $R_4$ is a phenyl radical,
X is an alkyl radical containing from 1 to 6 carbon atoms, a hydroxyl radical or a vinyl radical, n and p being an integer greater than or equal to 1, chosen so as to give the oil a weight-average molecular weight preferably less than 150 000 g/mol and more preferably less than 100 000 g/mol.
and a mixture thereof.

Preferably, the composition used in the context of the present invention comprises non-volatile phenyl silicone oil(s) not having a dimethicone fragment.

More particularly, the non-volatile phenyl silicone oils not having a dimethicone fragment are chosen from (I), with radicals R such that the silicone has no dimethicone fragment; (II) with radicals R such that the silicone has no dimethicone fragment, in particular formulae (III) and (III'); (V) with p=0; (VI) with p=0; (VII) with p=0; (VIII); (IX) with radicals R such that the silicone has no dimethicone fragment; or mixtures thereof.

Furthermore, preferably, the non-volatile phenyl silicone oils are chosen from those of formula (II), more particularly non-volatile phenyl silicone oils of formula (III) or (III').

In accordance with a particular embodiment of the invention, the content of non-volatile phenyl silicone oil(s) preferably not having a dimethicone fragment ranges from 1% to 8% by weight, preferably from 1.5% to 5% by weight, relative to the weight of the composition.

Additional Non-Volatile Oils
Non-Volatile Non-Phenyl Silicone Oils

The composition may optionally comprise at least one additional non-volatile oil, chosen from non-volatile non-phenyl silicone oils.

The expression "non-phenyl silicone oil" denotes a silicone oil not comprising phenyl substituents.

Representative examples of these non-volatile non-phenyl silicone oils which can be mentioned comprise polydimethylsiloxanes; alkyl dimethicones; vinyl methyl methicones; and also silicones modified with aliphatic groups and/or with functional groups, such as hydroxyl, thiol and/or amine groups, preferably hydroxyl groups.

It should be noted that "dimethicone" (INCI name) corresponds to a polydimethylsiloxane (chemical name).

In particular, these oils can be chosen from the following non-volatile oils:
polydimethylsiloxanes (PDMSs),
alkyl dimethicones comprising aliphatic groups, in particular alkyl or alkoxy groups, which are pendent and/or at the end of the silicone chain, these groups each comprising from 2 to 24 carbon atoms. Mention may be made, by way of example, of cetyl dimethicone, sold under the commercial reference Abil Wax 9801 from Evonik Goldschmidt,
PDMSs comprising functional groups, such as hydroxyl, thiol and/or amine groups, preferably hydroxyl groups,
polydimethylsiloxanes substituted with aliphatic groups, in particular $C_2$-$C_{24}$ groups, which are pendent and/or at the end of the silicone chain, and functional groups such as hydroxyl, thiol and/or amine groups, preferably hydroxyl groups,
polysiloxanes modified with fatty acids or fatty alcohols, and
mixtures thereof.

Preferably, these non-volatile non-phenyl silicone oils are chosen from polydimethylsiloxanes; alkyl dimethicones and also polydimethylsiloxanes substituted with aliphatic groups, in particular $C_2$-$C_{24}$ alkyl groups, and functional groups such as hydroxyl groups.

The non-volatile non-phenyl silicone oil can be chosen in particular from silicones of formula (I):

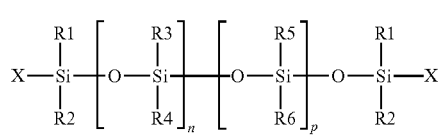

(I)

in which:
$R_1$, $R_2$, $R_5$ and $R_6$ are, together or separately, an alkyl radical containing 1 to 6 carbon atoms,
$R_3$ and $R_4$ are, together or separately, an alkyl radical containing 1 to 6 carbon atoms, or a hydroxyl radical,
X is an alkyl radical containing from 1 to 6 carbon atoms, a hydroxyl radical,
n and p are integers chosen so as to have a fluid compound, the viscosity of which at 25° C. is in particular between 8 centistokes (cSt) ($8\times10^{-6}$ $m^2$/s) and 100 000 cSt, and advantageously a weight-average molecular weight of less than or equal to 150 000 g/mol, preferably of less than or equal to 100 000 g/mol and better still of less than or equal to 10 000 g/mol.

There may be mentioned, as non-volatile non-phenyl silicone oils suitable for the implementation of the invention, those for which:
the $R_1$ to $R_6$ and X substituents represent a methyl group, and p and n are such that the viscosity is 60 000 cSt, for example the product sold under the name Dow Corning 200 Fluid 60 000 CS by Dow Corning and the product sold under the name Wacker Belsil DM 60 000 by Wacker,
the $R_1$ to $R_6$ and X substituents represent a methyl group, and p and n are such that the viscosity is 100 cSt or 350 cSt, for example the products sold respectively under the names Belsil DM100 and Dow Corning 200 Fluid 350 CS by Dow Corning, and
the $R_1$ to $R_6$ substituents represent a methyl group, the X group represents a hydroxyl group, and n and p are such that the viscosity is 700 cSt, for example the product sold under the name Baysilone Fluid T0.7 by Momentive.

Non-Polar Non-Volatile Hydrocarbon-Based Oils

The composition according to the invention may also comprise at least one additional non-polar non-volatile hydrocarbon-based oil.

These oils can be of plant, mineral or synthetic origin.

The term "non-polar hydrocarbon-based oil" is intended to mean, within the meaning of the present invention, an oil comprising only carbon and hydrogen atoms in its structure.

More particularly, the non-polar non-volatile hydrocarbon-based oils are chosen from linear or branched hydrocarbons of mineral or synthetic origin, such as:
liquid paraffin or derivatives thereof (mineral oil),
squalane,
isoeicosane,
naphthalene oil,
polybutenes, such as, for example, Indopol H-100, Indopol H-300 or Indopol H-1500 sold by the company Amoco,
polyisobutenes and hydrogenated polyisobutenes, such as, in particular, Parleam® products sold by the company Nippon Oil Fats, Panalane H-300 E sold by the company Amoco, Viseal 20000 sold by the company Synteal, Rewopal PIB 1000 sold by the company Witco or alternatively Parleam Lite sold by NOF Corporation,
decene/butene copolymers, polybutene/polyisobutene copolymers, especially Indopol L-14,
polydecenes and hydrogenated polydecenes, such as, in particular: Puresyn 10, Puresyn 150 or alternatively Puresyn 6 sold by the company ExxonMobil Chemicals,
and mixtures thereof.

If they are present in the composition used, then their content is such that the total content of non-volatile oils (in other words polar or non-polar, or phenyl or non-phenyl silicone hydrocarbon-based oils, having or not having at least one dimethicone fragment) varies between 6% and 20% by weight, preferably between 6% and 15% by weight, relative to the weight of the composition.

Non-Volatile Fluorinated Oils

The term "fluorinated oil" is intended to mean an oil containing at least one fluorine atom.

As examples of fluorinated oils, mention may be made of fluorosilicone oils, fluorinated polyethers, fluorosilicones in particular as described in document EP-A-847 752 and perfluorinated compounds.

Perfluorinated compounds is intended to mean, according to the invention, compounds in which all the hydrogen atoms have been replaced by fluorine atoms.

According to a preferred embodiment, the fluorinated oil is chosen from perfluorinated oils.

As examples of perfluorinated oils, mention may be made of perfluorodecalins and perfluoroperhydrophenanthrenes.

According to a preferred embodiment, the fluorinated oil is chosen from perfluoroperhydrophenanthrenes and in particular the Fiflow® products sold by Creations Couleurs. In particular, use may be made of the fluorinated oil for which the INCI name is Perfluoroperhydrophenanthrene, sold under the reference Fiflow 220 by the company F2 Chemicals.

Film-Forming Agent Comprising Carbosiloxane Dendrimer Unit(s)

Moreover, the composition according to the invention comprises at least one film-forming agent chosen from vinyl polymers comprising at least one carbosiloxane dendrimer-based unit.

More particularly, the content of film-forming agent(s) represents from 0.5% to 30% by weight of active material and preferably from 1% to 20% by weight, relative to the weight of the composition.

The term "film-forming" polymer is intended to mean a polymer that is capable of forming, by itself or in the presence of an auxiliary film-forming agent, a continuous deposit on a support, especially on keratin materials.

The vinyl polymer(s) have a backbone and at least one side chain, which comprises a carbosiloxane dendrimer-based unit having a carbosiloxane dendrimer structure.

In the context of the present invention, the term "carbosiloxane dendrimer structure" represents a molecular structure possessing branched groups having high molecular weights, said structure having high regularity in the radial direction starting from the bond to the backbone. Such carbosiloxane dendrimer structures are described in the form of a highly branched siloxane-silylalkylene copolymer in Japanese patent application JP 9-171 154.

A vinyl polymer according to the invention may contain units derived from carbosiloxane dendrimers that may be represented by the following general formula (I):

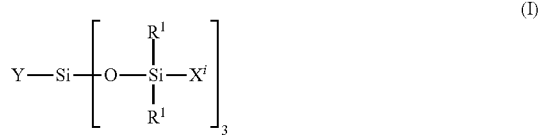

(I)

in which:
$R^1$ represents an aryl group having from 5 to 10 carbon atoms or an alkyl group having from 1 to 10 carbon atoms;

$X^i$ represents a silylalkyl group which, when i=1, is represented by formula (II):

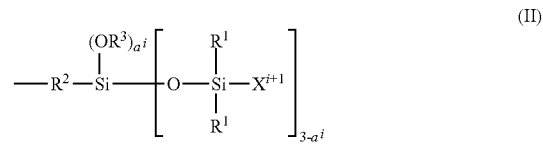

(II)

in which:
$R^1$ is as defined above in the formula (I), $R^2$ represents an alkylene radical having from 2 to 10 carbon atoms, $R^3$ represents an alkyl group having from 1 to 10 carbon atoms, $X^{i+i}$ is chosen from: a hydrogen atom, an alkyl group containing from 1 to 10 carbon atoms, an aryl group containing from 5 to 10 carbon atoms and a silylalkyl group defined above of formula (II) with i=i+1, i is an integer from 1 to 10 which represents the generation of said silylalkyl group, and $a^i$ is an integer from 0 to 3;

Y represents a radically polymerizable organic group chosen from:

organic groups comprising a methacrylic group or an acrylic group, said organic groups being represented by the formulae:

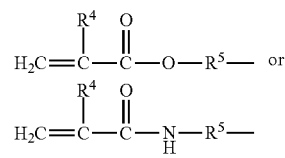

in which:
$R^4$ represents a hydrogen atom or an alkyl group having from 1 to 10 carbon atoms; and $R^5$ represents an alkylene group having from 1 to 10 carbon atoms, such as a methylene group, an ethylene group, a propylene group or a butylene group, methylene and propylene groups being preferred; and organic groups comprising a styryl group of formula:

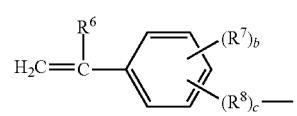

in which:
$R^6$ represents a hydrogen atom or an alkyl group having from 1 to 10 carbon atoms, such as a methyl group, an ethyl group, a propyl group or a butyl group, the methyl group being preferred;

$R^7$ represents an alkyl group having from 1 to 10 carbon atoms;

$R^8$ represents an alkylene group having from 1 to 10 carbon atoms, such as a methylene group, an ethylene group, a propylene group or a butylene group, the ethylene group being preferred;

b is an integer from 0 to 4; and c is 0 or 1, such that, if c is 0, $-(R^8)_c-$ represents a bond.

According to one embodiment, $R^1$ can represent an aryl group possessing from 5 to 10 carbon atoms or an alkyl group possessing from 1 to 10 carbon atoms. The alkyl group can preferably be represented by a methyl group, an ethyl group, a propyl group, a butyl group, a pentyl group, an isopropyl group, an isobutyl group, a cyclopentyl group or a cyclohexyl group. The aryl group can preferably be represented by a phenyl group and a naphthyl group. The methyl and phenyl groups are more particularly preferred, and the methyl group is most preferred.

According to one embodiment, $R^2$ represents an alkylene group possessing from 2 to 10 carbon atoms, in particular a linear alkylene group, such as an ethylene, propylene, butylene or hexylene group; or a branched alkylene group, such as a methylmethylene, methylethylene, 1-methylpentylene or 1,4-dimethylbutylene group.

The ethylene, methylethylene, hexylene, 1-methylpentylene and 1,4-dimethylbutylene groups are most preferred.

According to one embodiment, $R^3$ is chosen from methyl, ethyl, propyl, butyl and isopropyl groups.

In the formula (II), i indicates the number of generations and thus corresponds to the number of repetitions of the silylalkyl group.

For example, when the number of generations is equal to 1, the carbosiloxane dendrimer can be represented by the general formula shown below, in which Y, $R^1$, $R^2$ and $R^3$ are as defined above, $R^{12}$ represents a hydrogen atom or is identical to $R^1$ and $a^1$ is identical to $a^i$. Preferably, the total average number of $OR^3$ groups in a molecule is within the range from 0 to 7.

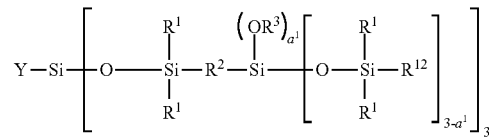

When the generation number is equal to 2, the carbosiloxane dendrimer may be represented by the general formula below, in which Y, $R^1$, $R^2$, $R^3$ and $R^{12}$ are the same as defined above; $a^1$ and $a^2$ represent the a' of the indicated generation. Preferably, the total average number of $OR^3$ groups in a molecule is within the range from 0 to 25.

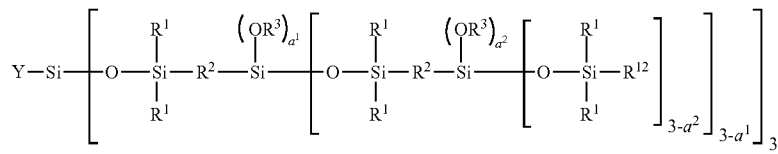

When the generation number is equal to 3, the carbosiloxane dendrimer is represented by the general formula below, in which Y, $R^1$, $R^2$, $R^3$ and $R^{12}$ are the same as defined above; $a^1$, $a^2$ and $a^3$ represent the $a^i$ of the indicated generation. Preferably, the total average number of $OR^3$ groups in a molecule is within the range from 0 to 79.

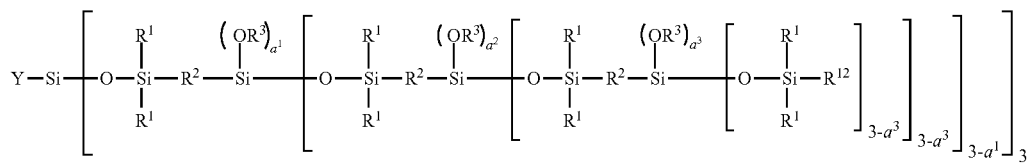

A vinyl polymer having at least one unit derived from carbosiloxane dendrimer has a molecular side chain containing a carbosiloxane dendrimer structure and can result from the polymerization of:

(A) from 0 to 99.9 parts by weight of a vinyl monomer, and
(B) from 100 to 0.1 parts by weight of a carbosiloxane dendrimer comprising a radically polymerizable organic group, represented by the general formula (I) as defined above.

The monomer of vinyl type which is the component (A) in the vinyl polymer having at least one unit derived from carbosiloxane dendrimer is a monomer of vinyl type which comprises a radically polymerizable vinyl group.

There is no particular limitation as regards such a monomer.

The following are examples of this monomer of vinyl type: methyl methacrylate, ethyl methacrylate, n-propyl methacrylate, isopropyl methacrylate or a methacrylate of lower alkyl analogue; glycidyl methacrylate; butyl methacrylate, butyl acrylate, n-butyl methacrylate, isobutyl methacrylate, tert-butyl acrylate, tert-butyl methacrylate, n-hexyl methacrylate, cyclohexyl methacrylate, 2-ethylhexyl acrylate, 2-ethylhexyl methacrylate, octyl methacrylate, lauryl methacrylate, stearyl acrylate, stearyl methacrylate or a higher methacrylate analogue; vinyl acetate, vinyl propionate or a vinyl ester of a lower fatty acid analogue; vinyl caproate, vinyl 2-ethylhexoate, vinyl laurate, vinyl stearate or a higher fatty acid ester analogue; styrene, vinyltoluene, benzyl methacrylate, phenoxyethyl methacrylate, vinylpyrrolidone or similar vinylaromatic monomers; methacrylamide, N-methylolmethacrylamide, N-methoxymethylmethacrylamide, isobutoxymethoxymethacrylamide, N,N-dimethylmethacrylamide or similar monomers of vinyl type containing amide groups; hydroxyethyl methacrylate, hydroxypropyl alcohol methacrylate or similar monomers of vinyl type containing hydroxyl groups; acrylic acid, methacrylic acid, itaconic acid, crotonic acid, fumaric acid, maleic acid or similar monomers of vinyl type containing a carboxylic acid group; tetrahydrofurfuryl methacrylate, butoxyethyl methacrylate, ethoxydiethylene glycol methacrylate, polyethylene glycol methacrylate, polypropylene glycol monomethacrylate, hydroxybutyl vinyl ether, cetyl vinyl ether, 2-ethylhexyl vinyl ether or a similar monomer of vinyl type with ether bonds; methacryloxypropyltrimethoxysilane, polydimethylsiloxane containing a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radically polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

Multifunctional monomers of vinyl type can also be used.

The following represent examples of such compounds: trimethylolpropane trimethacrylate, pentaerythrityl trimethacrylate, ethylene glycol dimethacrylate, tetraethylene glycol dimethacrylate, polyethylene glycol dimethacrylate, 1,4-butanediol dimethacrylate, 1,6-hexanediol dimethacrylate, neopentyl glycol dimethacrylate, ethoxylated trimethylolpropane trimethacrylate, tris(2-hydroxyethyl)isocyanurate dimethacrylate, tris(2-hydroxyethyl)isocyanurate trimethacrylate, polydimethylsiloxane capped with styryl groups possessing divinylbenzene groups on both ends, or analogous silicone compounds containing unsaturated groups.

A carbosiloxane dendrimer, which is the component (B), can be represented by the formula (I) as defined above.

The following represent the preferred examples of Y group of the formula (I): an acryloyloxymethyl group, a 3-acryloyloxypropyl group, a methacryloyloxymethyl group, a 3-methacryloyloxypropyl group, a 4-vinylphenyl group, a 3-vinylphenyl group, a 4-(2-propenyl)phenyl group, a 3-(2-propenyl)phenyl group, a 2-(4-vinylphenyl)ethyl group, a 2-(3-vinylphenyl)ethyl group, a vinyl group, an allyl group, a methallyl group and a 5-hexenyl group.

A carbosiloxane dendrimer according to the present invention may be represented by the formulae having the average structures below:

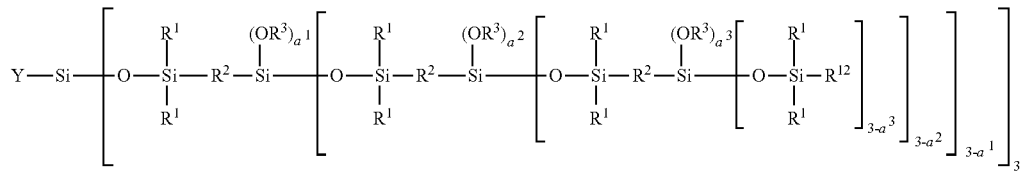

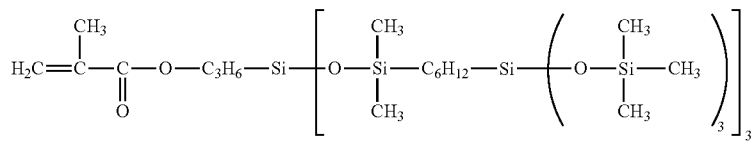

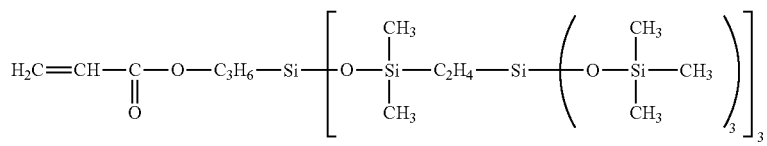

-continued
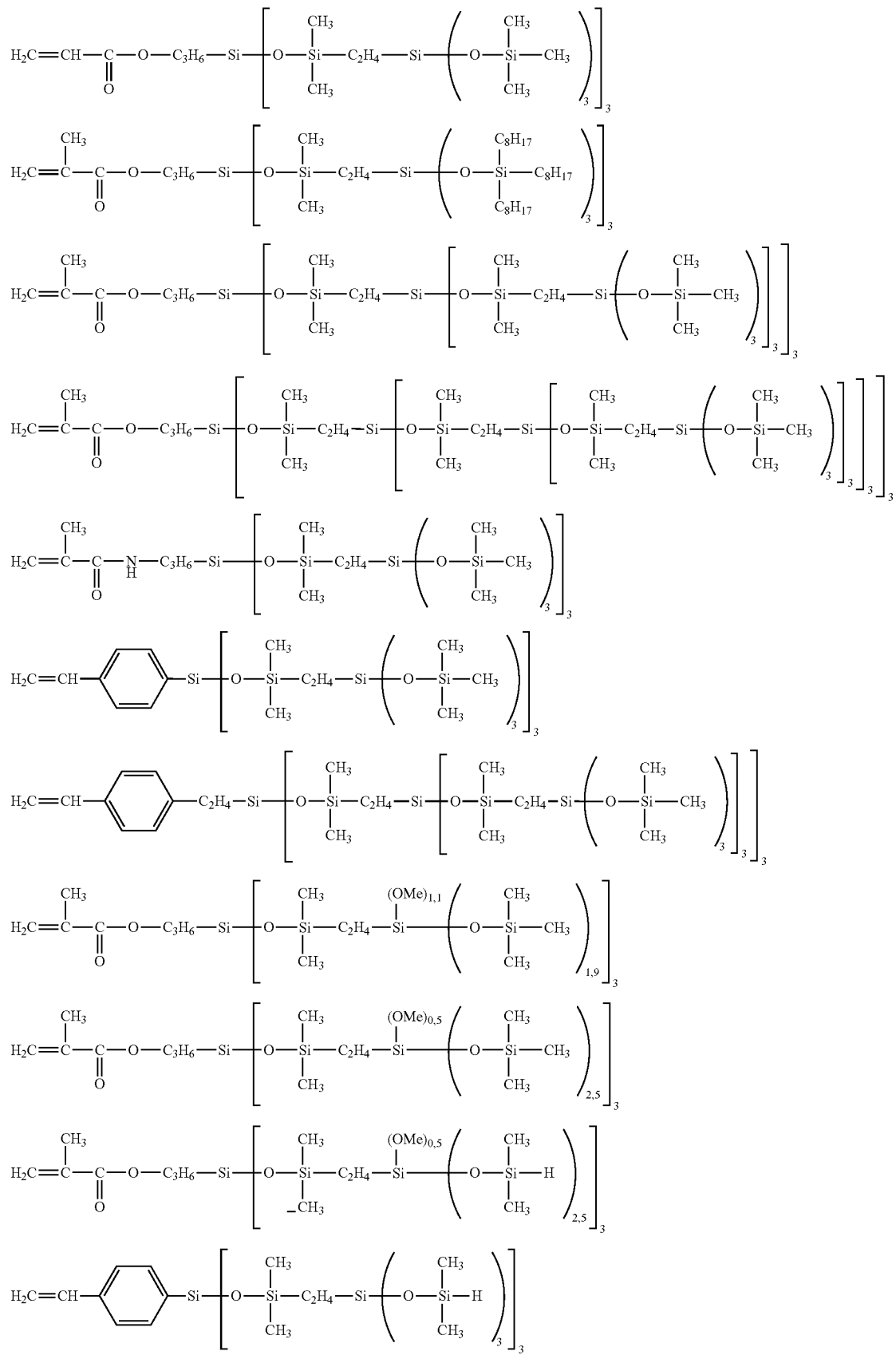

Thus, according to one embodiment, the carbosiloxane dendrimer of the composition according to the present invention is represented by the following formula:

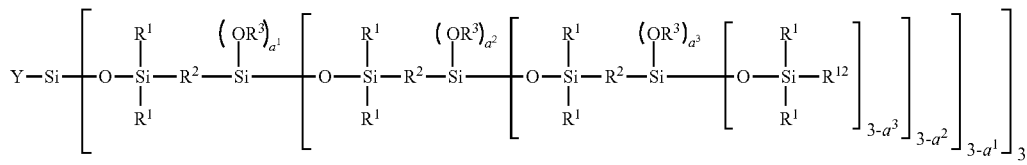

in which:
Y, $R^1$, $R^2$ and $R^3$ are as defined in the formulae (I) and (II) above;
$a^1$, $a^2$ and $a^3$ correspond to the definition of a' according to formula (II); and
$R^{12}$ is H, an aryl group having from 5 to 10 carbon atoms or an alkyl group having from 1 to 10 carbon atoms.

According to one embodiment, the carbosiloxane dendrimer of the composition according to the present invention is represented by one of the following formulae:

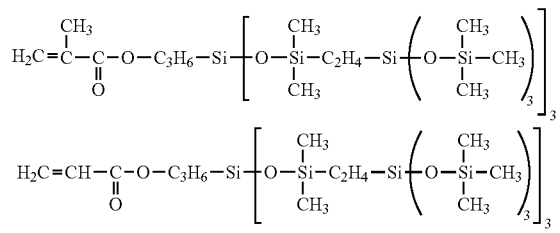

The vinyl polymer comprising the carbosiloxane dendrimer according to the invention can be manufactured according to the process for manufacturing a branched silalkylene siloxane described in Japanese Patent Application Hei 9-171 154.

To facilitate the preparation of starting material for cosmetic products, the number-average molecular weight of the vinyl polymer which comprises a carbosiloxane dendrimer can be chosen within the range between 3000 and 2 000 000 g/mol and preferably between 5000 and 800 000 g/mol. It can be a liquid, a gum, a paste, a solid, a powder or any other form. The preferred forms are solutions formed by the dilution of a dispersion or of a powder in solvents.

The vinyl polymer can be a dispersion of a polymer of vinyl type having a carbosiloxane dendrimer structure in its molecular side chain, in a liquid such as a silicone oil, an organic oil, an alcohol or water.

The silicone oil can be a dimethylpolysiloxane having the two molecular ends capped with trimethylsiloxy groups, a copolymer of methylphenylsiloxane and of dimethylsiloxane having the two molecular ends capped with trimethylsiloxy groups, a copolymer of methyl(3,3,3-trifluoropropyl)siloxane and of dimethylsiloxane having the two molecular ends capped with trimethylsiloxy groups, or analogous unreactive linear silicone oils, and also hexamethylcyclotrisiloxane, octamethylcyclotetrasiloxane, decamethylcyclopentasiloxane, dodecamethylcyclohexasiloxane or an analogous cyclic compound. In addition to the unreactive silicone oils, modified polysiloxanes containing functional groups such as silanol groups, amino groups and polyether groups on the ends or within the molecular side chains may be used.

The organic oils can be isododecane, liquid paraffin, isoparaffin, hexyl laurate, isopropyl myristate, myristyl myristate, cetyl myristate, 2-octyldodecyl myristate; isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cocoa oil, jojoba oil, gum oil, sunflower oil, soybean oil, camelia oil, squalane, castor oil, cottonseed oil, coconut oil, egg yolk oil, polypropylene glycol monooleate, neopentyl glycol 2-ethylhexanoate or an analogous glycol ester oil; triglyceryl isostearate, the triglyceride of a fatty acid of coconut oil, or an analogous oil of a polyhydric alcohol ester; polyoxyethylene lauryl ether, polyoxypropylene cetyl ether or an analogous polyoxyalkylene ether.

The alcohol may be any type that is suitable for use in combination with a cosmetic product starting material. For example, it can be methanol, ethanol, butanol, isopropanol or lower alcohol analogues.

A solution or a dispersion of the alcohol should have a viscosity within the range from 10 to $10^9$ mPa at 25° C. To improve the sensory use properties in a cosmetic product, the viscosity should be within the range from 100 to $5 \times 10^8$ mPa·s.

The solutions and dispersions can be easily prepared by mixing a vinyl polymer having at least one unit derived from carbosiloxane dendrimer with a silicone oil, an organic oil, an alcohol or water. The liquids can be present in the polymerization stage. In this case, the unreacted residual vinyl monomer should be completely removed by heat treatment of the solution or dispersion under atmospheric pressure or reduced pressure.

In the case of a dispersion, the dispersity of the polymer of vinyl type can be improved by adding a surfactant.

Such a surfactant can be hexylbenzenesulfonic acid, octylbenzenesulfonic acid, decylbenzenesulfonic acid, dodecylbenzenesulfonic acid, cetylbenzenesulfonic acid, myristylbenzenesulfonic acid or anionic surfactants of the sodium salts of these acids; octyltrimethylammonium hydroxide, dodecyltrimethylammonium hydroxide, hexadecyltrimethylammonium hydroxide, octyldimethylbenzylammonium hydroxide, decyldimethylbenzylammonium hydroxide, dioctadecyldimethylammonium hydroxide, (beef tallow)trimethylammonium hydroxide, (coconut oil)trimethylammonium hydroxide, or an analogous cationic surfactant; a polyoxyalkylene alkyl ether, a polyoxyalkylene alkylphenol, a polyoxyalkylene alkyl ester, the sorbitol ester of polyoxyalkylene, polyethylene glycol, polypropylene glycol, an ethylene oxide additive of diethylene glycol trimethylnonanol, and non-ionic surfactants of polyester type, and also mixtures.

In the dispersion, a mean particle diameter of the polymer of vinyl type can be within a range of between 0.001 and 100 microns and preferably between 0.01 and 50 microns. The reason for this is that, outside the recommended range, a cosmetic product mixed with the emulsion will not have a nice enough feel on the lips or to the touch, nor sufficient spreading properties nor a pleasant feel.

A vinyl polymer contained in the dispersion or the solution may have a concentration in the range between 0.1% and 95% by weight and preferably between 5% and 85% by weight. However, to facilitate the handling and the preparation of the mixture, the range should preferably be between 10% and 75% by weight.

A vinyl polymer suitable for the invention can also be one of the polymers described in the examples of patent application EP 0 963 751.

According to a preferred embodiment, a vinyl polymer grafted with a carbosiloxane dendrimer may be the product of polymerization of:

(A1) from 0 to 99.9 parts by weight of one or more acrylate or methacrylate monomer(s); and (B1) from 100 to 0.1 parts by weight of an acrylate or methacrylate monomer of a tris[tri(trimethylsiloxy)silylethyldimethylsiloxy]silylpropyl carbosiloxane dendrimer.

The monomers (A1) and (B1) correspond respectively to specific monomers (A) and (B).

According to one embodiment, a vinyl polymer bearing at least one carbosiloxane dendrimer-based unit may comprise a tris[tri(trimethylsiloxy)silylethyldimethylsiloxy]-silylpropyl carbosiloxane dendrimer-based unit corresponding to one of the formulae:

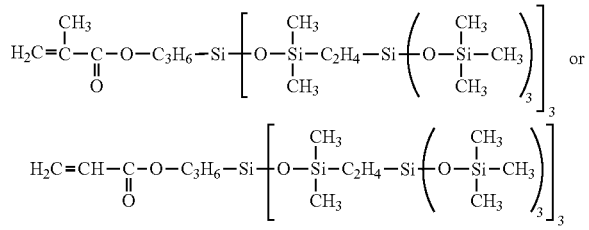

According to a preferred mode, a vinyl polymer bearing at least one carbosiloxane dendrimer-based unit used in the invention comprises at least one butyl acrylate monomer.

According to one embodiment, a vinyl polymer may also comprise at least one fluorinated organic group.

Structures in which the polymerized vinyl units constitute the backbone and carbosiloxane dendritic structures and also fluorinated organic groups are attached to side chains are particularly preferred.

The fluorinated organic groups can be obtained by replacing with fluorine atoms all or some of the hydrogen atoms of methyl, ethyl, propyl, isopropyl, butyl, isobutyl, tert-butyl, pentyl, neopentyl, hexyl, cyclohexyl, heptyl, octyl, nonyl, decyl, undecyl, dodecyl, tridecyl, tetradecyl, hexadecyl and octadecyl groups and of other alkyl groups of 1 to 20 carbon atoms, and also alkyloxyalkylene groups of 6 to 22 carbon atoms.

The groups represented by the formula $—(CH_2)_x—(CF_2)_y—R^{13}$ are suggested as examples of fluoroalkyl groups obtained by substituting fluorine atoms for hydrogen atoms of alkyl groups. In the formula, the subscript "x" is 0, 1, 2 or 3, and "y" is an integer from 1 to 20. $R^{13}$ is an atom or a group chosen from a hydrogen atom, a fluorine atom, $—CH(CF_3)_2—$ or $CF(CF_3)_2$. Such fluorine-substituted alkyl groups are exemplified by linear or branched polyfluoroalkyl or perfluoroalkyl groups represented by the formulae presented below: $—CF_3$, $—C_2F_5$, $-nC_3F_7$, $—CF(CF_3)_2$, $-nC_4F_9$, $CF_2CF(CF_3)_2$, $-nC_5F_{11}$, $-nC_6F_{13}$, $-nC_8F_{17}$, $CH_2CF_3$, $—(CH(CF_3)_2$, $CH_2CH(CF_3)_2—CH_2(CF_2)_2F$, $—CH_2(CF_2)_3F$, $—CH_2(CF_2)_4F$, $CH_2(CF_2)_6F$, $CH_2(CF_2)_8F$, $—CH_2CH_2CF_3$, $—CH_2CH_2(CF_2)_2F$, $—CH_2CH_2(CF_2)_3F$, $—CH_2CH_2(CF_2)_4F$, $—CH_2CH_2(CF_2)_6F$, $—CH_2CH_2(CF_2)_9F$, $—CH_2CH_2(CF_2)_{10}F$, $—CH_2CH_2(CF_2)_{12}F$, $CH_2CH_2(CF_2)_{14}F$, $—CH_2CH_2(CF_2)_{16}F$, $—CH_2CH_2CH_2CF_3$, $—CH_2CH_2CH_2(CF_2)_2F$, $—CH_2CH_2CH_2(CF_2)_2H$, $—CH_2(CF_2)_4H$ and $—CH_2CH_2(CF_2)_3H$.

The groups represented by $—CH_2CH_2—(CF_2)_m—CFR^{14}—[OCF_2CF(CF_3)]_n—OC_3F_7$ are suggested as fluoroalkyloxyfluoroalkylene groups obtained by substituting fluorine atoms for hydrogen atoms of alkyloxyalkylene groups. In the formula, the subscript "m" is 0 or 1, "n" is 0, 1, 2, 3, 4 or 5, and $R^{14}$ is a fluorine atom or $CF_3$. Such fluoroalkyloxyfluoroalkylene groups are exemplified by the perfluoroalkyloxyfluoroalkylene groups represented by the formulae presented below: $—CH_2CH_2CF(CF_3)—[OCF_2CF(CF_3)]_n—OC_3F_7$, $—CH_2CH_2CF_2CF_2—[OCF_2CF(CF_3)]_n—OC_3F_7$.

The number-average molecular weight of the vinyl polymer used in the present invention may be between 3000 and 2 000 000 g/mol and more preferably between 5000 and 800 000 g/mol.

This type of fluorinated vinyl polymer can be obtained by addition:
- of a vinyl monomer (M2) without a fluorinated organic group,
- to a vinyl monomer (M1) comprising fluorinated organic groups, and
- a carbosiloxane dendrimer (B) as defined above, of general formula (I) as defined above, by subjecting them to a copolymerization.

Thus, according to one embodiment, a composition of the invention can comprise a vinyl polymer having at least one unit derived from carbosiloxane dendrimer and resulting from the copolymerization of a vinyl monomer (M1) as defined above, optionally of a vinyl monomer (M2) as defined above, and of a carbosiloxane dendrimer (B) as defined above, said vinyl polymer having a copolymerization ratio of the monomer (M1) to the monomer (M2) of 0.1 to 100:99.9 to 0% by weight, and a copolymerization ratio of the sum of the monomers (M1) and (M2) to the monomer (B) of 0.1 to 99.9:99.9 to 0.1% by weight.

The vinyl monomers (M1) comprising fluorinated organic groups in the molecule are preferably monomers represented by the general formula:

$(CH^2)=CR^{15}COOR^f$.

In this formula, $R^{15}$ is a hydrogen atom or a methyl group and $R^1$ is a fluorinated organic group exemplified by the fluoroalkyl and fluoroalkyloxyfluoroalkylene groups described above. The compounds represented by the formulae presented below are suggested as specific examples of the component (M1). In the formulae present below, "z" is an integer from 1 to 4.

$CH_2=CCH_3COO—CF_3$, $CH_2=CCH_3COO—C_2F_5$, $CH_2=CCH3COO-nC_3F_7$, $CH_2=CCH_3COO—CF(CF_3)_2$, $CH_2=CCH_3COO-nC_4F_9$, $CH_2=CCH_3COO—CF(CF_3)_2$, $CH_2=CCH_3COO-nC_5F_{11}$, $CH_2=CCH_3COO-nC_6F_{13}$, $CH_2=CCH_3COO-nC_8F_{17}$, $CH_2=CCH_3COO—CH_2CF_3$, $CH_2=CCH_3COO—CH(CF_3)_2$, $CH_2=CCH_3COO—CH_2CH(CF_3)_2$, $CH_2=CCH_3COO—CH_2(CF_2)_2F$, $CH_2=CCH_3COO—CH_2(CF_2)_2F$, $CH_2=CCH_3COO—CH_2(CF_2)_4F$, $CH_2=CCH_3COO—CH_2(CF_2)_6F$, $CH_2=CCH_3COO—CH_2(CF_2)_8F$, $CH_2=CCH_3COO—CH_2CH_2CF_3$, $CH_2=CCH_3COO—CH_2CH_2(CF_2)_2F$, $CH_2=CCH_3COO—CH_2CH_2(CF_2)_3F$, $CH_2=CCH_3COO—CH_2CH_2(CF_2)_4F$, $CH_2=CCH_3COO—CH_2CH_2(CF_2)_6F$,

CH₂=CCH₃COO—CH₂CH₂(CF₂)₈F, CH₂=CCH₃COO—CH₂CH₂(CF₂)₁₀F, CH₂=CCH₃COO—CH₂CH₂(CF₂)₁₂F, CH₂=CCH₃COO—CH₂CH₂(CF₂)₁₄F,
CH₂=CCH₃COO—CH₂—CH₂—(CF₂)₁₆F,
CH₂=CCH₃COO—CH₂CH₂CH₂CF₃,
CH₂=CCH₃COO—CH₂CH₂CH₂(CF₂)₂F,
CH₂=CCH₃COO—CH₂CH₂CH₂(CF₂)₂H,
CH₂=CCH₃COO—CH₂(CF₂)₄H, CH₂=CCH₃COO—(CF₂)₃H, CH₂=CCH₃COO—CH₂CH₂CF(CF₃)—[OCF₂—CF(CF₃)]z-OC₃F₇, CH₂=CCH₃COO—CH₂CH₂CF₂CF₂—[OCF₂—CF(CF₃)]z-OC₃F₇, CH₂=CHCOO—CF₃, CH₂=CHCOO—C₂F₅, CH₂=CHCOO-nC₃F₇, CH₂=CHCOO—CF(CF₃)₂, CH₂=CHCOO-nC₄F₉, CH₂=CHCOO—CF₂CF(CF₃)₂, CH₂=CHCOO-nC₅F₁₁, CH₂=CHCOO-nC₆F₁₃, CH₂=CHCOO-nC₈F₁₇, CH₂=CHCOO—CH₂CF₃, CH₂=CHCOO—CH(CF₃)₂, CH₂=CHCOO—CH₂CH(CF₃)₂, CH₂=CHCOO—CH₂(CF₂)₂F, CH₂=CHCOO—CH₂(CF₂)₃F, CH₂=CHCOO—CH₂(CF₂)₄F, CH₂=CHCOO—CH₂(CF₂)₆F, CH₂=CHCOO—CH₂(CF₂)₈F, CH₂=CHCOO—CH₂CH₂CF₃, CH₂=CHCOO—CH₂CH₂(CF₂)₂F, CH₂=CHCOO—CH₂CH₂(CF₂)₃F, CH₂=CHCOO—CH₂CH₂(CF₂)₄F, CH₂=CHCOO—CH₂CH₂(CF₂)₆F, CH₂=CHCOO—CH₂CH₂(CF₂)₈F, CH₂=HCOO—CH₂CH₂(CF₂)₁₀F, CH₂=CHCOO—CH₂CH₂—(CF₂)₁₂F, CH₂=CHCOO—CH₂CH₂(CF₂)₁₄F, CH₂=CHCOO—CH₂CH₂—(CF₂)₁₆F, CH₂=CHCOO—CH₂CH₂(CF₂)₃F, CH₂=CHCOO—CH₂CH₂CH₂(CF₂)₂F, CH₂=CHCOO—CH₂CH₂CH₂(CF)H, CH₂=CHCOO—CH₂(CF₂)₄H, CH₂=CHCOO—CH₂CH₂(CF₂)₃H, CH₂=CHCOO—CH₂CH₂CF(CF₃)—, [OCF₂—CF(CF₃)]z—OC₃F₇, CH₂=CHCOO—CH₂CH₂CF₂CF₂(CF₃)—[OCF₂—CF(CF₃)]₂—OC₃F₇.

Among these, the vinyl polymers represented by the formulae presented below are preferred:
CH₂=CHCOO—CH₂CH₂(CF₂)₆F, CH₂=CHCOO—CH₂CH₂(CF₂)₈F, CH₂=CCH₃COO—CH₂CH₂(CF₂)₆F, CH₂=CCH₃COO—CH₂CH₂(CF₂)₈F, CH₂=CHCOO—CH₂CF₃, CH₂=CCH₃COO—CH₂CF₃.

The vinyl polymers represented by the formulae presented below are particularly preferred:
CH₂=CHCOO—CH₂CF₃, CH₂=CCHCOO—CH₂CF₃.

The vinyl monomers (M2) which do not comprise fluorinated organic groups in the molecule can be any monomers having radically polymerizable vinyl groups which are exemplified, for example, by methyl acrylate, methyl methacrylate, ethyl acrylate, ethyl methacrylate, n-propyl acrylate, n-propyl methacrylate, isopropyl acrylate, isopropyl methacrylate and other lower alkyl acrylates or methacrylates; glycidyl acrylate, glycidyl methacrylate; n-butyl acrylate, n-butyl methacrylate, isobutyl acrylate, isobutyl methacrylate, tert-butyl acrylate, tert-butyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate, stearyl acrylate, stearyl methacrylate and other higher acrylates and methacrylates; vinyl acetate, vinyl propionate and other lower fatty acid vinyl esters; vinyl butyrate, vinyl caproate, vinyl 2-ethylhexanoate, vinyl laurate, vinyl stearate and other higher fatty acid esters; styrene, vinyltoluene, benzyl acrylate, benzyl methacrylate, phenoxyethyl acrylate, phenoxyethyl methacrylate, vinylpyrrolidone and other vinylaromatic monomers; dimethylaminoethyl acrylate, dimethylaminoethyl methacrylate, diethylaminoethyl acrylate, diethylaminoethyl methacrylate and other aminovinyl monomers, acrylamide, methacrylamide, N-methylolacrylamide, N-methylolmethacrylamide, N-methoxymethylacrylamide, N-methoxymethyl-methacrylamide, isobutoxymethoxyacrylamide, isobutoxymethoxymethacrylamide, N,N-dimethylacrylamide, N,N-dimethylmethacrylamide and other vinylamide monomers; hydroxyethyl acrylate, hydroxyethyl methacrylate, acrylic acid hydroxypropyl alcohol, methacrylic acid hydroxypropyl alcohol and other hydroxyvinyl monomers; acrylic acid, methacrylic acid, itaconic acid, crotonic acid, fumaric acid, maleic acid and other vinylcarboxylic acid monomers; tetrahydrofurfuryl acrylate, tetrahydrofurfuryl methacrylate, butoxyethyl acrylate, butoxyethyl methacrylate, ethoxydiethylene glycol acrylate, ethoxydiethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether and other vinyl monomers having ether bonds; acryloyloxypropyltrimethoxysilane, methacryloyloxypropyltrimethoxysilane, polydimethylsiloxanes comprising acryloyl or methacryloyl groups at one of the ends, polydimethylsiloxanes comprising alkenylaryl groups at one of the ends and other silicone compounds having unsaturated groups; butadiene; vinyl chloride; vinylidene chloride, acrylonitrile, methacrylonitrile; dibutyl fumarate; maleic anhydride; dodecylsuccinic anhydride; acryl glycidyl ether, methacryl glycidyl ether, 3,4-epoxycyclohexylmethyl acrylate, 3,4-epoxycyclohexylmethyl methacrylate, alkali metal salts, ammonium salts and organic amine salts of acrylic acid, of methacrylic acid, of itaconic acid, of crotonic acid, of fumaric acid, of maleic acid and of other radically polymerizable unsaturated carboxylic acids, radically polymerizable unsaturated monomers comprising sulfonic acid groups, such as styrenesulfonic acid, and also their alkali metal salts, their ammonium salts and their organic amine salts; the quaternary ammonium salts resulting from acrylic acid or methacrylic acid, such as 2-hydroxy-3-methacryloyloxypropyltrimethylammonium chloride, methacrylic acid esters of a tertiary amine alcohol, such as the diethylamine ester of methacrylic acid, and their quaternary ammonium salts.

In addition, it is also possible to use, as vinyl monomers (M2), the polyfunctional vinyl monomers which are exemplified, for example, by trimethylolpropane triacrylate, trimethylolpropane trimethacrylate, pentaerythrityl triacrylate, pentaerythrityl trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropane ethoxylate triacrylate, trimethylolpropane ethoxylate trimethacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane, the two ends of the molecular chain of which are blocked with alkenylaryl groups, and other silicone compounds having unsaturated groups.

As regards the abovementioned ratio in which (M1) and (M2) are copolymerized, the ratio by weight of (M1) to (M2) is preferably within the range from 1:99 to 100:0.

Y can be chosen, for example, from organic groups having acrylic or methacrylic groups, organic groups having an alkenylaryl group, or alkenyl groups with from 2 to 10 carbon atoms.

The organic groups having acrylic or methacrylic groups and the alkenylaryl groups are as defined above.

Mention may be made, among the compounds (B), for example, of the following compounds:

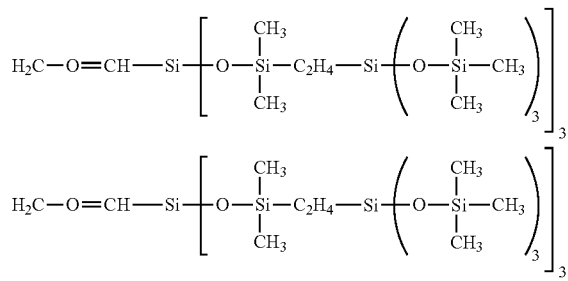

The carbosiloxane dendrimers (B) can be prepared using the process for preparing branched siloxane/silalkylene copolymers described in the document EP 1 055 674.

For example, they can be prepared by subjecting organic alkenyl silicone compounds and silicone compounds comprising hydrogen atoms bonded to the silicon, represented by the formula (IV) as defined above, to a hydrosilylation reaction.

The copolymerization ratio (by weight) of the monomer (B) to the monomers (M1) and (M2) is preferably within the range from 1:99 to 99:1 and even more preferably within the range from 5:95 to 95:5.

Amino groups can be introduced into the side chains of the vinyl polymer using, included in the component (M2), vinyl monomers comprising amino groups, such as dimethylaminoethyl acrylate, dimethylaminoethyl methacrylate, diethylaminoethyl acrylate and diethylaminoethyl methacrylate, followed by performing a modification with potassium acetate monochloride, ammonium acetate monochloride, the aminomethylpropanol salt of monochloroacetic acid, the triethanolamine salt of monobromoacetic acid, sodium monochloropropionate, and other alkali metal salts of halogenated fatty acids; otherwise, carboxylic acid groups can be introduced into the side chains of the vinyl polymer using, included in the component (M2), vinyl monomers comprising carboxylic acids, such as acrylic acid, methacrylic acid, itaconic acid, crotonic acid, fumaric acid and maleic acid, and the like, followed by neutralizing the product with triethylamine, diethylamine, triethanolamine and other amines.

A fluorinated vinyl polymer can be one of the polymers described in the examples of application WO 03/045337.

According to a preferred embodiment, a vinyl polymer grafted in the sense of the present invention may be conveyed in an oil or a mixture of oils, which are preferably volatile, chosen in particular from silicone oils and hydrocarbon-based oils, and mixtures thereof.

According to a particular embodiment, a silicone oil that is suitable for use in the invention may be cyclopentasiloxane.

According to another particular embodiment, a hydrocarbon-based oil that is suitable for use in the invention may be isododecane.

The vinyl polymers grafted with at least one carbosiloxane dendrimer-based unit that may be particularly suitable for the present invention are the polymers of which the INCI name is Acrylates/Polytrimethylsiloxy Methacrylate Copolymer, and which are in particular sold under the names FA 4002 ID Silicone Acrylate and FA 4001 CM Silicone Acrylate, by the company Dow Corning.

According to one embodiment, the composition according to the present invention comprises the vinyl polymer having at least one carbosiloxane dendrimer-based unit in an active material content of from 0.5% to 20%, in particular from 1% to 15%, more particularly from 1.5% to 10% and preferably from 3% to 5% by weight, relative to the weight of said composition.

Surfactants

According to a particular embodiment of the invention, the composition comprises at least one surfactant.

A surfactant or a mixture of surfactants may be present at from 0.05% to 20% by weight and preferably from 0.5% to 10% by weight, relative to the weight of the composition.

More particularly, the suitable surfactants may be chosen from non-ionic, anionic, cationic and amphoteric surfactants, and mixtures thereof.

For the choice of these surfactants, reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of this reference, for anionic and non-ionic surfactants.

Surfactants Promoting Direct Emulsions (Oil-in-Water; O/W)

Among the suitable surfactants promoting oil-in-water emulsions, mention may be made of the compounds which follow.

Non-Ionic Surfactants

In particular, at least one emulsifying surfactant having at 25° C. an HLB (hydrophilic-lipophilic balance) within the Griffin sense of greater than or equal to 8 may be used. The HLB value according to Griffin is defined in J. Soc. Cosm. Chem. 1954 (volume 5), pages 249-256.

An emulsifying surfactant having at 25° C. an HLB balance (hydrophilic-lipophilic balance) within the Griffin sense of less than 8 may also optionally be used.

The non-ionic surfactants may be chosen especially from alkyl and polyalkyl esters of poly(ethylene oxide), oxyalkylenated alcohols, alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, and optionally polyoxyethylenated alkyl and polyalkyl ethers of glycerol, and mixtures thereof.

1) Alkyl and polyalkyl esters of poly(ethylene oxide) that are preferably used are those with a number of ethylene oxide (EO) units ranging from 2 to 200. Examples that may be mentioned include stearate 40 EO, stearate 50 EO, stearate 100 EO, laurate 20 EO, laurate 40 EO and distearate 150 EO.

2) Alkyl and polyalkyl ethers of poly(ethylene oxide) that are preferably used are those with a number of ethylene oxide (EO) units ranging from 2 to 200. Examples that may be mentioned include cetyl ether 23 EO, oleyl ether 50 EO, phytosterol 30 EO, stearteh 40, stearteh 100 and beheneth 100.

3) Oxyalkylenated, in particular oxyethylenated and/or oxypropylenated, alcohols that are preferably used are those that can comprise from 1 to 150 oxyethylene and/or oxypropylene units, in particular containing from 20 to 100 oxyethylene units, in particular ethoxylated fatty alcohols, in particular of $C_8$-$C_{24}$ and preferably of $C_{12}$-$C_{18}$, such as stearyl alcohol ethoxylated with 20 oxyethylene units (CTFA name Steareth-20), for instance Brij 78 sold by the company Uniqema, cetearyl alcohol ethoxylated with 30 oxyethylene units (CTFA name Ceteareth-30), and the mixture of $C_{12}$-$C_{15}$ fatty alcohols comprising 7 oxyethylene units (CTFA name $C_{12-15}$ Pareth-7), for instance the product sold under the name Neodol 25-7® by Shell Chemicals; or in particular oxyalkylenated (oxyethylenated and/or oxypropylenated) alcohols containing from 1 to 15 oxyethylene and/or oxypropylene units, in particular ethoxylated $C_8$-$C_{24}$ and preferably $C_{12}$-$C_{18}$ fatty alcohols, such as stearyl alcohol ethoxylated with 2 oxyethylene units (CTFA name Steareth-2), for instance Brij 72 sold by the company Uniqema.

4) Optionally polyoxyethylenated alkyl and polyalkyl esters of sorbitan that are preferably used are those with a number of ethylene oxide (EO) units ranging from 0 to 100. Examples that may be mentioned include sorbitan laurate 4 or 20 EO, in particular polysorbate 20 (or polyoxyethylene (20) sorbitan monolaurate) such as the product Tween 20 sold by the company Uniqema, sorbitan palmitate 20 EO, sorbitan stearate 20 EO, sorbitan oleate 20 EO, or else the Cremophor products (RH 40, RH 60, etc.) from BASF.

5) Optionally polyoxyethylenated alkyl and polyalkyl ethers of sorbitan that are preferably used are those with a number of ethylene oxide (EO) units ranging from 0 to 100.

6) Alkyl and polyalkyl glucosides or polyglucosides that are preferably used are those containing an alkyl group comprising from 6 to 30 carbon atoms and preferably from 6 to 18 or even from 8 to 16 carbon atoms, and containing a glucoside group preferably comprising from 1 to 5 and in particular 1, 2 to 3 glucoside units. The alkylpolyglucosides may be chosen, for example, from decylglucoside ($C_9$/$C_{11}$ alkylpolyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, for instance the product sold under the name Plantacare KE 3711® by the company Cognis or Oramix CG 110® by the company SEPPIC; laurylglucoside, for instance the product sold under the name Plantacare 1200 UP® by the company Henkel or Plantaren 1200 N® by the company Henkel; cocoglucoside, for instance the product sold under the name Plantacare 818 UP® by the company Henkel; caprylylglucoside, for instance the product sold under the name Plantacare 810 UP® by the company Cognis; and mixtures thereof.

More generally, the surfactants of alkylpolyglycoside type are defined more specifically hereinbelow.

7) Examples of alkyl and polyalkyl esters of sucrose that may be mentioned are Crodesta F150, sucrose monolaurate sold under the name Crodesta SL 40, and the products sold by Ryoto Sugar Ester, for instance sucrose palmitate sold under the reference Ryoto Sugar Ester P1670, Ryoto Sugar Ester LWA 1695 or Ryoto Sugar Ester 01570.

8) Optionally polyoxyethylenated alkyl and polyalkyl esters of glycerol that are preferably used are those with a number of ethylene oxide (EO) units ranging from 0 to 100 and a number of glycerol units ranging from 1 to 30. Examples that may be mentioned include hexaglyceryl monolaurate and PEG-30 glyceryl stearate.

9) Optionally polyoxyethylenated alkyl and polyalkyl ethers of glycerol that are preferably used are those with a number of ethylene oxide (EO) units ranging from 0 to 100 and a number of glycerol units ranging from 1 to 30. Examples that may be mentioned include Nikkol Batyl Alcohol 100 and Nikkol Chimyl Alcohol 100.

Anionic Surfactants

The anionic surfactants may be chosen from alkyl ether sulfates, carboxylates, amino acid derivatives, sulfonates, isethionates, taurates, sulfosuccinates, alkylsulfoacetates, phosphates and alkyl phosphates, polypeptides, metal salts of $C_{10}$-$C_{30}$ and especially $C_{12}$-$C_{20}$ fatty acids, in particular metal stearates, and mixtures thereof.

1) Examples of alkyl ether sulfates that may be mentioned include sodium lauryl ether sulfate (70/30 $C_{12}$-$C_{14}$) (2.2 EO) sold under the names Sipon AOS225 or Texapon N702 by the company Henkel, ammonium lauryl ether sulfate (70/30 $C_{12}$-$C_{14}$) (3 EO) sold under the name Sipon LEA 370 by the company Henkel, ammonium ($C_{12}$-$C_{14}$) alkyl ether (9 EO) sulfate sold under the name Rhodapex AB/20 by the company Rhodia Chimie, and the mixture of sodium magnesium lauryl oleyl ether sulfate sold under the name Empicol BSD 52 by the company Albright & Wilson.

2) Examples of carboxylates that may be mentioned include salts (for example alkali metal salts) of N-acylamino acids, glycol carboxylates, amido ether carboxylates (AECs) and polyoxyethylenated carboxylic acid salts.

The surfactant of glycol carboxylate type may be chosen from alkyl glycol carboxylics or 2-(2-hydroxyalkyloxyacetate), salts thereof and mixtures thereof. These alkyl glycol carboxylics comprise a linear or branched, saturated or unsaturated, aliphatic and/or aromatic alkyl chain containing from 8 to 18 carbon atoms. These carboxylics may be neutralized with mineral bases such as potassium hydroxide or sodium hydroxide.

Examples of surfactants of glycol carboxylic type that may be mentioned include sodium lauryl glycol carboxylate or sodium 2-(2-hydroxyalkyloxy acetate) such as the product sold under the name Beaulight Shaa® by the company Sanyo, Beaulight LCA-25N® or the corresponding acid form Beaulight Shaa (Acid form)®.

An example of an amido ether carboxylate (AEC) that may be mentioned is sodium lauryl amido ether carboxylate (3 EO) sold under the name Akypo Foam 30° by the company Kao Chemicals.

Examples of polyoxyethylenated carboxylic acid salts that may be mentioned include oxyethylenated (6 EO) sodium lauryl ether carboxylate (65/25/10 $C_{12-14-16}$) sold under the name Akypo Soft 45 NV® by the company Kao Chemicals, polyoxyethylenated and carboxymethylated fatty acids of olive oil origin sold under the name Olivem 400® by the company Biologia e Tecnologia, and oxyethylenated (6 EO) sodium tridecyl ether carboxylate sold under the name Nikkol ECTD-6NEX® by the company Nikkol.

3) Amino acid derivatives that may especially be mentioned include alkaline salts of amino acids, such as:
  sarcosinates, for instance the sodium lauroyl sarcosinate sold under the name Sarkosyl NL 97® by the company Ciba or sold under the name Oramix L30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;
  alaninates, for instance sodium N-lauroyl N-methyl amidopropionate sold under the name Sodium Nikkol Alaninate LN 30® by the company Nikkol, or sold under the name Alanone ALE® by the company Kawaken, and triethanolamine N-lauroyl N-methyl alanine sold under the name Alanone Alta® by the company Kawaken;

glutamates, for instance triethanolamine monococoyl glutamate sold under the name Acylglutamate CT-12® by the company Ajinomoto, or triethanolamine lauroyl glutamate sold under the name Acylglutamate LT-12® by the company Ajinomoto.

The glutamic acid salts and/or derivatives are described more specifically hereinbelow.

aspartates, for instance the mixture of triethanolamine N-lauroyl aspartate and of triethanolamine N-myristoyl aspartate, sold under the name Asparack® by the company Mitsubishi;

glycine derivatives (glycinates), for instance the sodium N-cocoyl glycinate sold under the names Amilite GCS-12® and Amilite GCK 12 by the company Ajinomoto;

citrates, such as the oxyethylenated (9 mol) citric monoester of cocoyl alcohols sold under the name Witconol EC 1129 by the company Goldschmidt;

galacturonates, such as the sodium dodecyl-D-galactoside uronate sold by the company Soliance.

4) Examples of sulfonates that may be mentioned include alpha-olefin sulfonates, for instance the sodium alpha-olefin sulfonate ($C_{14-16}$) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, and the sodium secondary olefin sulfonate sold under the name Hostapur SAS 30® by the company Clariant.

5) Isethionates that may be mentioned include acylisethionates, for instance sodium cocoylisethionate, such as the product sold under the name Jordapon CI P® by the company Jordan.

6) Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

7) Examples of sulfosuccinates that may be mentioned include the oxyethylenated (3 EO) lauryl alcohol monosulfosuccinate (70/30 $C_{12}/C_{14}$) sold under the names Setacin 103 Special® and Rewopol SB-FA 30 K 4° by the company Witco, the disodium salt of a $C_{12}$-$C_{14}$ alcohol hemisulfosuccinate, sold under the name Setacin F Special Paste® by the company Zschimmer Schwarz, the oxyethylenated (2 EO) disodium oleamidosulfosuccinate sold under the name Standapol SH 135° by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50° by the company Witco, and the ricinoleic monoethanolamide monosulfosuccinate sold under the name Rewoderm S 1333° by the company Witco. Polydimethylsiloxane sulfosuccinates may also be used, such as disodium PEG-12 dimethicone sulfosuccinate sold under the name Mackanate-DC30 by the company MacIntyre.

8) Examples of alkyl sulfoacetates that may be mentioned include the mixture of sodium lauryl sulfoacetate and disodium lauryl ether sulfosuccinate, sold under the name Stepan-Mild LSB by the company Stepan.

9) Examples of phosphates and alkyl phosphates that may be mentioned include monoalkyl phosphates and dialkyl phosphates, such as the lauryl monophosphate sold under the name MAP 20° by the company Kao Chemicals, the potassium salt of dodecylphosphoric acid, mixture of monoester and diester (predominantly diester), sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

10) The polypeptides are obtained, for example, by condensation of a fatty chain onto amino acids from cereal and in particular from wheat and oat. Examples of polypeptides that may be mentioned include the potassium salt of hydrolysed lauroyl wheat protein, sold under the name Aminofoam W OR by the company Croda, the triethanolamine salt of hydrolysed cocoyl soybean protein, sold under the name May-Tein SY by the company Maybrook, the sodium salt of lauroyl oat amino acids, sold under the name Proteol Oat by the company SEPPIC, collagen hydrolysate grafted onto coconut fatty acid, sold under the name Geliderm 3000 by the company Deutsche Gelatine, and soybean proteins acylated with hydrogenated coconut acids, sold under the name Proteol VS 22 by the company SEPPIC.

11) As metal salts of $C_{10}$-$C_{30}$ and especially $C_{12}$-$C_{20}$ fatty acids, mention may be made in particular of metal stearates, such as sodium stearate and potassium stearate, and also polyhydroxystearates.

Cationic Surfactants

The cationic surfactants may be chosen from:
alkylimidazolidiniums such as isostearylethylimidonium ethosulfate,
ammonium salts, such as ($C_{12-30}$ alkyl)tri($C_{1-4}$ alkyl) ammonium halides, for instance N,N,N-trimethyl-1-docosanaminium chloride (or behentrimonium chloride).

Amphoteric Surfactants

The compositions according to the invention may also contain one or more amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

Silicone Surfactants

According to a second embodiment, the composition comprises at least one silicone surfactant. Examples that may be mentioned include:

a) as non-ionic surfactants with an HLB of greater than or equal to 8 at 25° C., used alone or as a mixture; mention may be made in particular of:
dimethicone copolyol, such as the product sold under the name Q2-5220® by the company Dow Corning;
dimethicone copolyol benzoate, such as the product sold under the names Finsolv SLB 101® and 201® by the company Fintex;

b) as non-ionic surfactants with an HLB of less than 8 at 25° C., used alone or as a mixture, mention may be made in particular of:

the mixture of cyclomethicone/dimethicone copolyol sold under the name Q2-3225C® by the company Dow Corning.

Surfactants Promoting Inverse Emulsions (Water-in-Oil; W/O)

As emulsifying surfactants that may be used for the preparation of the W/O emulsions, examples that may be mentioned include sorbitan alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Goldschmidt, and the mixture of cetyldimethicone copolyol, of polyglyceryl isostearate (4 mol) and of hexyl laurate, sold under the name Abil WE O9 by the company Goldschmidt, or else phosphated surfactants.

One or more coemulsifiers, which may be chosen advantageously from the group comprising polyol alkyl esters, may also be added thereto.

Polyol alkyl esters that may in particular be mentioned include polyethylene glycol esters, for instance PEG-30 dipolyhydroxystearate, such as the product sold under the name Arlacel P135 by the company ICI.

A crosslinked elastomeric solid organopolysiloxane comprising at least one oxyalkylene group, such as the products obtained according to the procedure of Examples 3, 4 and 8 of document U.S. Pat. No. 5,412,004 and the examples of document U.S. Pat. No. 5,811,487, in particular the product of Example 3 (synthetic example) of patent U.S. Pat. No. 5,412,004, and such as the product sold under the reference KSG 21 by the company Shin-Etsu, may also be used as surfactants for W/O emulsions.

According to one particularly preferred embodiment, an emulsion according to the invention, in particular a W/O emulsion, comprises at least one silicone surfactant, more particularly chosen from dimethicone copolyols.

A dimethicone copolyol that may be used according to the invention is an oxypropylenated and/or oxyethylenated polydimethylmethylsiloxane.

Dimethicone copolyols that may be used are those corresponding more particularly to formula (II) below:

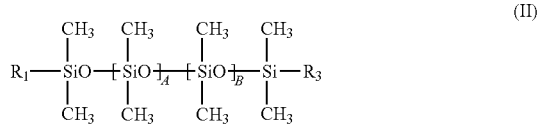

(II)

in which:
$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, a $C_1$-$C_3$ alkyl radical or a $C_2$-$C_4$ acyl radical;
A is an integer ranging from 0 to 200;
B is an integer ranging from 0 to 50; on condition that A and B are not simultaneously equal to zero;
x is an integer ranging from 1 to 6;
y is an integer ranging from 1 to 30; and
z is an integer ranging from 0 to 30, preferably 20.

According to one preferred embodiment, in the compound of formula (II), $R_1$=$R_3$=methyl radical, x is an integer ranging from 2 to 6 and y is an integer ranging from 4 to 30. $R_4$ is in particular a hydrogen.

Examples of compounds of formula (II) that may be mentioned include the compounds of formula (III):

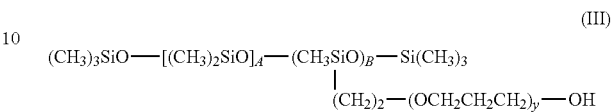

(III)

in which A is an integer ranging from 20 to 105, B is an integer ranging from 2 to 10 and y is an integer ranging from 10 to 20.

Examples of silicone compounds of formula (II) that may also be mentioned include the compounds of formula (IV):

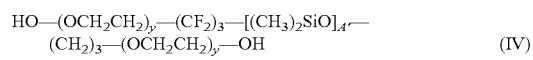

(IV)

in which A' and y are integers ranging from 10 to 20.

Dimethicone copolyols that may be used include those sold under the names DC 5329, DC 7439-146, DC 2-5695 and Q4-3667 by the company Dow Corning; KF-6013, KF-6015, KF-6016, KF-6017, KF-6028 and KF-6050 L by the company Shin-Etsu.

The compounds DC 5329, DC 7439-146 and DC 2-5695 are compounds of formula (III) in which, respectively, A is 22, B is 2 and y is 12; A is 103, B is 10 and y is 12; A is 27, B is 3 and y is 12.

According to a particular embodiment, the silicone surfactant may be PEG polydimethylsiloxyethyl dimethicone, sold in particular by the company Shin-Etsu under the reference KF-6028, PEG-10 dimethicone sold in particular by the company Shin-Etsu under the reference KF-6017, and mixtures thereof.

The surfactant may also be chosen from non-ionic surfactants of the type of monoglycerolated or polyglycerolated fatty alcohols which can be represented by formula (V) below:

in which:
R represents a linear or branched, saturated or unsaturated radical comprising from 8 to 40 carbon atoms and preferably from 10 to 30 carbon atoms;
m represents a number ranging from 1 to 10.

As compounds of this type, mention may be made of lauryl alcohol comprising 4 mol of glycerol, isostearyl alcohol comprising 4 mol of glycerol, lauryl alcohol comprising 1.5 mol of glycerol, oleyl alcohol comprising 4 mol of glycerol, oleyl alcohol comprising 2 mol of glycerol, cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The fatty alcohol can represent a mixture of fatty alcohols in the same way that the value of m represents a statistical value, which means that, in a commercial product, several types of polyglycerolated fatty alcohols can coexist in the form of a mixture.

Preferably, whatever the direction of the emulsion, the surfactant(s) is (are) chosen from non-ionic surfactants and silicone surfactants, or mixtures thereof.

Volatile Oils

According to one particular embodiment of the invention, the composition comprises at least one volatile oil.

The volatile oil(s) may be chosen from hydrocarbon-based oils, silicone oils and fluorinated oils, and mixtures thereof.

The volatile hydrocarbon-based oils are preferably chosen from non-polar hydrocarbon-based oils and may in particular be chosen from volatile hydrocarbon-based oils having from 8 to 16 carbon atoms and mixtures thereof, and in particular:
- branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Permethyl,
- linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture (Cétiol UT), the mixtures of n-undecane ($C_{11}$) and of n-tridecane ($C_{13}$) obtained in Examples 1 and 2 of patent application WO 2008/155 059 from the company Cognis, and
- mixtures thereof.

The volatile silicone oils can be chosen from silicone oils with a flash point ranging from 40° C. to 102° C., preferably with a flash point of greater than 55° C. and less than or equal to 95° C., and preferentially ranging from 65° C. to 95° C.

As volatile silicone oils that may be used in the invention, mention may be made of linear or cyclic silicones with a viscosity at 25° C. of less than 8 centistokes (cSt) ($8 \times 10^{-6}$ m$^2$/s), and in particular containing from 2 to 10 silicon atoms and in particular from 2 to 7 silicon atoms, these silicones optionally comprising alkyl or alkoxy groups containing from 1 to 10 carbon atoms.

As volatile silicone oil(s) that may be used in the invention, mention may be made especially of dimethicones with viscosities of 2, 5 and 6 cSt, octamethylcyclotetrasiloxane, decamethylcyclopentasiloxane, dodecamethylcyclohexa-siloxane, heptamethylhexyltrisiloxane, heptamethyloctyltrisiloxane, hexamethyldi-siloxane, octamethyltrisiloxane, decamethyltetrasiloxane and dodecamethyl-pentasiloxane, and mixtures thereof.

The volatile oils can also be chosen from a fluorinated oil, such as nonafluoromethoxybutane or perfluoromethylcyclopentane, and mixtures thereof.

Preferably, the composition according to the invention comprises at least one volatile oil, more particularly chosen from non-polar volatile hydrocarbon-based oils, from volatile silicone oils, alone or as mixtures.

According to one particular embodiment, the composition comprises at least one volatile oil in a content ranging from 5% to 45% by weight, in particular from 10% to 30% by weight, relative to the weight of said composition.

Aqueous Phase

The composition according to the invention comprises water and optionally at least one water-soluble solvent (the whole constituting the aqueous phase).

For the purposes of the present invention, the term "water-soluble solvent" is intended to mean a compound that is liquid at 25° C. and atmospheric pressure, and that is water-miscible (miscibility with water of greater than 50% by weight at 25° C. and atmospheric pressure).

Among the water-soluble solvents that may be used in the compositions in accordance with the invention, mention may be made in particular of monoalcohols containing from 1 to 5 carbon atoms, such as preferably ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The composition according to the invention preferentially comprises at least 20% by weight of aqueous phase (water+water-soluble solvent(s)), in particular from 20% to 60% by weight and especially from 25% to 50% by weight, relative to the weight of the composition.

The composition according to the invention preferentially comprises at least 15% by weight, in particular from 20% to 60% by weight and especially from 25% to 50% by weight of water, relative to the weight of the composition.

According to one embodiment, the composition may comprise at least 60% by weight, preferably at least 70% by weight and in particular at least 75% by weight of water, relative to the total weight of the aqueous phase.

According to a preferred embodiment, the composition comprises a total content of aqueous phase and volatile oil(s) of greater than or equal to 50% by weight and in particular greater than or equal to 60% by weight relative to the weight of the composition.

Dyestuffs:

A composition in accordance with the present invention may comprise at least one dyestuff, which may be chosen from water-soluble or water-insoluble, liposoluble or non-liposoluble, organic or inorganic dyestuffs, and materials with an optical effect, and mixtures thereof.

For the purposes of the present invention, the term "dyestuff" is intended to mean a compound that is capable of producing a coloured optical effect when it is formulated in a sufficient amount in a suitable cosmetic medium.

The water-soluble colorants used according to the invention are more particularly water-soluble dyes.

For the purposes of the invention, the term "water-soluble dye" is intended to mean any natural or synthetic, generally organic compound, which is soluble in an aqueous phase or water-miscible solvents and which is capable of colouring. In particular, the term "water-soluble" is intended to characterize the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the invention, mention may be made in particular of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As non-limiting illustrations of sources of water-soluble dyestuff(s) that may be used in the context of the present invention, mention may be made especially of those of natural origin, such as extracts of carmine of cochineal, of beetroot, of grape, of carrot, of tomato, of annatto, of paprika, of henna, of caramel and of curcumin.

Thus, the water-soluble dyestuffs that are suitable for use in the invention are especially carminic acid, betanin, anthocyans, enocyanins, lycopene, beta-carotene, bixin, norbixin, capsanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble dyestuffs are in particular permitted for food use. Representatives of these dyes that may be mentioned more particularly include dyes of the carotenoid family, referenced under the food codes E120, E162, E163, E160a-g, E150a, E101, E100, E140 and E141.

According to a particularly preferred embodiment, the water-soluble dyestuff(s) are chosen from the disodium salt of brilliant yellow FCF sold by the company LCW under the name DC Yellow 6, the disodium salt of fuchsin acid D sold by the company LCW under the name DC Red 33, and the trisodium salt of Rouge Allura sold by the company LCW under the name FD & C Red 40.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

Organic lakes are organic pigments formed from a dye attached to a substrate.

The lakes, which are also known as organic pigments, may be chosen from the materials below, and mixtures thereof:
  cochineal carmine;
  organic pigments of azo dyes, anthraquinone dyes, indigoid dyes, xanthene dyes, pyrene dyes, quinoline dyes, triphenylmethane dyes or fluoran dyes. Mention may in particular be made, among the organic pigments, of those known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 or FD&C Yellow No. 6;
  the organic lakes can be insoluble sodium, potassium, calcium, barium, aluminium, zirconium, strontium or titanium salts of acid dyes, such as azo, anthraquinone, indigoid, xanthene, pyrene, quinoline, triphenylmethane or fluoran dyes, these dyes possibly comprising at least one carboxylic or sulfonic acid group.

The organic lakes can also be supported by an organic support, such as rosin or aluminium benzoate, for example.

Mention may in particular be made, among the organic lakes, of those known under the following names: D&C Red No. 2 Aluminium lake, D&C Red No. 3 Aluminium lake, D&C Red No. 4 Aluminium lake, D&C Red No. 6 Aluminium lake, D&C Red No. 6 Barium lake, D&C Red No. 6 Barium/Strontium lake, D&C Red No. 6 Strontium lake, D&C Red No. 6 Potassium lake, D&C Red No. 7 Aluminium lake, D&C Red No. 7 Barium lake, D&C Red No. 7 Calcium lake, D&C Red No. 7 Calcium/Strontium lake, D&C Red No. 7 Zirconium lake, D&C Red No. 8 Sodium lake, D&C Red No. 9 Aluminium lake, D&C Red No. 9 Barium lake, D&C Red No. 9 Barium/Strontium lake, D&C Red No. 9 Zirconium lake, D&C Red No. 10 Sodium lake, D&C Red No. 19 Aluminium lake, D&C Red No. 19 Barium lake, D&C Red No. 19 Zirconium lake, D&C Red No. 21 Aluminium lake, D&C Red No. 21 Zirconium lake, D&C Red No. 22 Aluminium lake, D&C Red No. 27 Aluminium lake, D&C Red No. 27 Aluminium/Titanium/Zirconium lake, D&C Red No. 27 Barium lake, D&C Red No. 27 Calcium lake, D&C Red No. 27 Zirconium lake, D&C Red No. 28 Aluminium lake, D&C Red No. 30 lake, D&C Red No. 31 Calcium lake, D&C Red No. 33 Aluminium lake, D&C Red No. 34 Calcium lake, D&C Red No. 36 lake, D&C Red No. 40 Aluminium lake, D&C Blue No. 1 Aluminium lake, D&C Green No. 3 Aluminium lake, D&C Orange No. 4 Aluminium lake, D&C Orange No. 5 Aluminium lake, D&C Orange No. 5 Zirconium lake, D&C Orange No. 10 Aluminium lake, D&C Orange No. 17 Barium lake, D&C Yellow No. 5 Aluminium lake, D&C Yellow No. 5 Zirconium lake, D&C Yellow No. 6 Aluminium lake, D&C Yellow No. 7 Zirconium lake, D&C Yellow No. 10 Aluminium lake, FD&C Blue No. 1 Aluminium lake, FD&C Red No. 4 Aluminium lake, FD&C Red No. 40 Aluminium lake, FD&C Yellow No. 5 Aluminium lake or FD&C Yellow No. 6 Aluminium lake.

Mention may also be made of liposoluble dyes, such as, for example, Sudan Red, DC Red 17, DC Green 6, β-carotene, soybean oil, Sudan Brown, DC Yellow 11, DC Violet 2, DC Orange 5 or quinoline yellow.

The chemical substances corresponding to each of the organic colorants cited above are mentioned in the publication "International Cosmetic Ingredient Dictionary and Handbook", 1997 edition, pages 371 to 386 and 524 to 528, published by The Cosmetic, Toiletry, and Fragrance Association, the content of which is incorporated into the present patent application by reference.

The pigments may also have been subjected to a hydrophobic treatment.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids; N-acylated amino acids or salts thereof; lecithin, isopropyl triisostearyl titanate, and mixtures thereof.

The N-acylated amino acids can comprise an acyl group having from 8 to 22 carbon atoms, such as, for example, a 2-ethylhexanoyl, caproyl, lauroyl, myristoyl, palmitoyl, stearoyl or cocoyl group. The salts of these compounds can be aluminium, magnesium, calcium, zirconium, zinc, sodium or potassium salts. The amino acid can, for example, be lysine, glutamic acid or alanine.

The term "alkyl" cited in the abovementioned compounds denotes in particular an alkyl group having from 1 to 30 carbon atoms and preferably having from 5 to 16 carbon atoms.

Hydrophobic treated pigments are described in particular in application EP-A-1 086 683.

Within the meaning of the present patent application, "nacre" is intended to mean coloured particles of any shape, which are or are not iridescent, produced in particular by certain molluscs in their shells or else synthesized, and which exhibit a colour effect via optical interference.

Mention may be made, as examples of nacres, of pearlescent pigments, such as titanium mica covered with an iron oxide, mica covered with bismuth oxychloride, titanium mica covered with chromium oxide, titanium mica covered with an organic dye, in particular of the abovementioned type, and also pearlescent pigments based on bismuth oxychloride.

They may also be mica particles, at the surface of which are superposed at least two successive layers of metal oxides and/or of organic colorants.

The nacres may more particularly have a yellow, pink, red, bronze, orangey, brown, gold and/or coppery colour or glint.

As illustrations of nacres that may be introduced as interference pigments into the first composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper glint sold in particular by the company Engelhard under the name Copper 340A (Timica); the nacres with a red glint sold in particular by the company Merck under the name Sienna fine (17386) (Colorona); the nacres with a yellow glint sold in particular by the company Engelhard under the name Yellow (4502) (Chromalite); the red nacres with a gold glint sold in particular by the company Engelhard under the name Sunstone G012 (Gemtone); the pink nacres sold in particular by the company Engelhard under the name Tan opale 0005 (Gemtone); the black nacres with a gold glint sold in particular by the company Engelhard under the name Nu antique bronze 240 AB (Timica), the blue nacres sold in particular by the company Merck under the name Matte blue (17433) (Microna), the white nacres with a silvery glint sold in particular by the company Merck under the name Xirona Silver, and the golden-green pink-orange nacres sold in particular by the company Merck under the name Indian summer (Xirona), and mixtures thereof.

Additives

The composition according to the invention may also comprise any additive chosen by those skilled in the art such that the advantageous properties intrinsically associated with the compositions in accordance with the invention are not, or not substantially, adversely affected by the envisaged addition(s).

As additives that may be incorporated into the compositions in accordance with the invention, mention may be made especially of hydrophilic thickeners, hydrophobic thickeners, fillers of organic or mineral nature, stabilizers, preserving agents, sweeteners, cosmetic active agents, flavourings or fragrances, pigment dispersers, and film-forming agents other than those according to the invention.

As cosmetic active agents, mention may be made of sunscreens, vitamins A, E, C and B3, provitamins such as D-panthenol, calmatives such as α-bisabolol, Aloe vera, allantoin, plant extracts or essential oils, protective or restructuring agents, refreshing agents such as menthol and derivatives thereof, emollients, moisturizers, antiwrinkle active agents and essential fatty acids, and mixtures thereof.

As examples of hydrophilic thickening polymers, mention may be made more particularly of:

homopolymers or copolymers of acrylic acid or methacrylic acid, or salts thereof and esters thereof, and in particular the products sold under the names Versicol F or Versicol K by the company Allied Colloid, Ultrahold 8 by the company Ciba-Geigy, and polyacrylic acids of Synthalen K type, and salts, in particular sodium salts, of polyacrylic acid (corresponding to the INCI name sodium acrylate copolymer) and more particularly a crosslinked sodium polyacrylate (corresponding to the INCI name sodium acrylate copolymer (and) caprylic/capric triglyceride) sold under the name Luvigel EM by the company BASF, copolymers of acrylic acid and of acrylamide sold in the form of the sodium salt thereof under the name Reten by the company Hercules, the sodium polymethacrylate sold under the name Darvan No. 7 by the company Vanderbilt, and the sodium salts of polyhydroxycarboxylic acids sold under the name Hydagen F by the company Henkel, polyacrylic acid/alkyl acrylate copolymers, preferably modified or unmodified carboxyvinyl polymers, particularly with acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol EDT 2020, and even more preferentially Pemulen TR-2, polyacrylamidomethylpropanesulfonic acid partially neutralized with aqueous ammonia and highly crosslinked, sold by the company Clariant, acrylamidopropanesulfonic/acrylamide copolymers of Sepigel or Simulgel type sold by the company SEPPIC, polyoxyethylenated acrylamidopropanesulfonic/alkyl methacrylate copolymers (crosslinked or non-crosslinked) of the Aristoflex HMS type sold by the company Clariant, copolymers of hydroxyalkylacrylic acid or salts thereof and of acryloyldimethyl taurate monomers such as the product Sepinov EMT 10 sold by the company SEPPIC, and mixtures thereof.

Other examples of hydrophilic gelling polymers that may be mentioned include:

anionic, cationic, amphoteric or non-ionic chitin or chitosan polymers;

cellulose polymers, for instance alkylcelluloses such as hydroxyethylcellulose, hydroxypropylcellulose, hydroxymethylcellulose, ethylhydroxyethylcellulose and carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

optionally modified polymers of natural origin, such as galactomannans and derivatives thereof, for instance konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan gum and derivatives thereof;

alginates and carrageenans;

muccopolysaccharides such as hyaluronic acid;

and mixtures thereof.

If the composition comprises any, the content of hydrophilic thickener ranges from 0.01% to 3% by weight, preferably from 0.05% to 2% by weight and more advantageously from 0.1% to 1% by weight relative to the weight of the composition.

By way of hydrophobic thickeners, mention may most particularly be made of hydrophobic mineral thickeners such as modified clays, modified silicas, or mixtures thereof.

Hydrophobic Modified Clays

Clays are silicates containing a cation which can be chosen from calcium, magnesium, aluminium, sodium, potassium or lithium cations, and mixtures thereof.

Mention may be made, as examples of such products, of clays of the family of the smectites, and also of the family of the vermiculites, stevensite or chlorites. These clays may be of natural or synthetic origin.

Preferably, use is made of organophilic clays, more particularly of modified clays, such as montmorillonite, bentonite, hectorite, attapulgite or sepiolite, and mixtures thereof. The clay is preferably a bentonite or a hectorite.

These clays are modified with a chemical compound chosen from quaternary amines, tertiary amines, amine acetates, imidazolines, amine soaps, fatty sulfates, alkylarylsulfonates or amine oxides, and mixtures thereof.

Mention may thus be made of hectorites modified by a quaternary amine, more specifically by a $C_{10}$ to $C_{22}$ fatty acid ammonium halide, such as chloride, comprising or not comprising an aromatic group, such as hectorite modified by a distearyldimethylammonium halide, preferably chloride (CTFA name: Disteardimonium hectorite), such as, for example, that sold under the name Bentone 38V, Bentone 38V CG or Bentone EW CE by Elementis, or stearalkonium hectorites, such as in particular the product Bentone 27 V.

Mention may also be made of quaternium-18 bentonites, such as those sold, inter alia, under the names Bentone 34 by the company Elementis, Claytone 40, Tixogel VP by the company United Catalyst by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as those sold under the name Claytone HT by the company Southern Clay.

According to a preferred embodiment, the thickening agent is chosen from organophilic modified clays, in particular organophilic modified hectorites, in particular modified by benzyldimethylammonium stearate or distearyldimethylammonium halides, in particular chlorides.

Modified Silicas

Mention may also be made of fumed silica hydrophobically treated at the surface, the size of the particles of which is advantageously less than 1 μm. This is because it is possible to chemically modify the surface of the silica, by chemical reaction generating a reduction in the number of silanol groups present at the surface of the silica. It is especially possible to substitute silanol groups with hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as Silica Silylate according to the CTFA (6th edition, 1995). They are sold, for example, under the references Aerosil R812® by the company Degussa and Cab-O-Sil TS-530® by the company Cabot, dimethylsilyloxyl or polydimethylsiloxane groups, which are obtained especially by treating fumed silica in the presence of polydimethylsiloxane, for example hexamethyldisiloxane, or dimethyldichlorosilane. Silicas thus treated are known as Silica Dimethyl Silylate according to the CTFA (6th edition, 1995). They are sold, for example, under the references Aerosil R972® and Aerosil R974® by the company Degussa and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

The composition according to the invention can also comprise at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. Drying of this type makes it possible to avoid contraction of the pores and of the material. The sol-gel process and the various drying operations are described in detail in Brinker C. J. and Scherer G. W., Sol-Gel Science, New York, Academic Press, 1990.

The hydrophobic silica aerogel particles suitable for the implementation of the invention exhibit a specific surface area per unit mass ($S_M$) ranging from 500 to 1500 m²/g, preferably from 600 to 1200 m²/g and better still from 600 to 800 m²/g, and a size, expressed as the volume-average diameter (D[0.5]), ranging from 1 to 1500 μm, better still from 1 to 1000 μm, preferably from 1 to 100 μm, in particular from 1 to 30 μm, more preferably from 5 to 25 μm, better still from 5 to 20 μm and even better still from 5 to 15 μm.

According to an advantageous embodiment, the hydrophobic silica aerogel particles used in the present invention have a specific surface area per unit mass ($S_M$) ranging from 600 to 800 m²/g and a size expressed as the volume-average diameter (D[0.5]) ranging from 5 to 20 μm and even better still from 5 to 15 μm.

The specific surface area per unit mass may be determined by the nitrogen absorption method, known as the BET (Brunauer-Emmett-Teller) method, described in The Journal of the American Chemical Society, vol. 60, page 309, February 1938 and corresponding to international standard ISO 5794/1 (annex D). The BET specific surface corresponds to the total specific surface of the particles under consideration.

The sizes of the silica aerogel particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of non-spherical particles, an "effective" particle diameter. This theory is in particular described in the publication by Van de Hulst, H. C., Light Scattering by Small Particles, Chapters 9 and 10, Wiley, New York, 1957.

According to a preferred embodiment, the hydrophobic silica aerogel particles used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$.

The aerogels used according to the present invention are hydrophobic silica aerogels, preferably aerogels of silyl silica (INCI name: silica silylate).

As regards the preparation of hydrophobic silica aerogel particles modified at the surface by silylation, reference may be made to the document U.S. Pat. No. 7,470,725.

Use will preferably be made of hydrophobic silica aerogel particles modified at the surface by trimethylsilyl groups.

As hydrophobic silica aerogels that may be used in the invention, examples that may be mentioned include the aerogel sold under the name VM-2260 (INCI name: Silica silylate), by the company Dow Corning, the particles of which have an average size of about 1000 microns and a specific surface area per unit mass ranging from 600 to 800 m$^2$/g.

Mention may also be made of the aerogels sold by Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica silylate) by the company Dow Corning, the particles of which have an average size ranging from 5-15 microns and a specific surface area per unit mass ranging from 600 to 800 m$^2$/g.

Preferably, the mineral thickeners are chosen from organophilic clays, in particular modified hectorites; hydrophobic treated fumed silica; hydrophobic silica aerogels, or mixtures thereof, and more specifically still at least one organophilic modified clay or at least one hydrophobic modified silica, in particular an organophilic modified clay.

More particularly, if the composition contains it (them), the content of mineral thickener(s) represents from 0.2% to 2.5% by weight, expressed as active material, and preferably from 0.5% to 2% by weight, relative to the weight of the composition.

The example hereinafter is given as a non-limiting illustration of the field of the invention.

EXAMPLE

1. Composition

The composition of which the ingredients are collated in the table below is prepared; the amounts are expressed in weight amount of starting material:

| Phase | Ingredient | Composition 1 | Composition 2 |
|---|---|---|---|
| A | Cetyl PEG/PPG-10/1 Dimethicone (ABIL EM 90 sold by Evonik Goldschmidt) | 3 | 3 |
| | Polyglyceryl-4 Isostearate (Isolan GI34 sold by Evonik Goldschmidt) | 1 | 1 |
| | PEG/PPG-18/18 Dimethicone (KF6050L sold by Shin Etsu) | 0.3 | 0.3 |
| | Isododecane | 2.7 | 2.7 |
| | Dodecamethylpentasiloxane (Xiameter PMX-200 Silicone Fluid 2CS; sold by Dow Corning) | 11.5 | 10.5 |
| | Trimethyl pentaphenyl trisiloxane (Dow Corning PH-1555 HRI Cosmetic Fluid sold by Dow Corning) | 2.2 | 2.2 |
| | 2-Octyldodecanol | 10 | 15 |
| | Acrylates/polytrimethylsiloxy methacrylate copolymer (Dow Corning FA 4002 ID silicone acrylate sold by Dow Corning, as a 40% by weight mixture in isododecane) | 10 | 10 |
| B | Disteardimonium hectorite | 1 | 1 |
| | Propylene carbonate | 0.3 | 0.3 |
| | Dodecamethylpentasiloxane (Xiameter PMX-200 Silicone Fluid 2CS; sold by Dow Corning) | 3.7 | 3.7 |
| C | Red 7 | 1.5 | 0.9 |
| | Red 28 Lake | 1.3 | 0.6 |
| | Anatase titanium oxide coated with aluminium stearoyl glutamate (97/3) | 1.8 | 0.9 |
| | black iron oxide coated with aluminium stearoyl glutamate (3%) | 1.4 | 0.7 |
| | Yellow 6 Lake | 2.1 | 1 |
| D | Water | 34.5 | 34.5 |
| | Butylene glycol | 6 | 6 |
| | Magnesium sulfate | 0.7 | 0.7 |
| | Ethanol | 5 | 5 |

2. Preparation

First of all, the pigments are mixed into a part of the dodecamethylpentasiloxane of phase A (in an Exakt three-roll machine).

Separately, the aqueous phase D is prepared using a magnetic bar.

Separately, the ingredients of phase B are mixed by means of a Rayneri mixer.

The ingredients of phase A, the pigments/dodecamethylcyclopentasiloxane mixture previously obtained are then mixed, with Moritz stirring, for 20 minutes, at ambient temperature.

Once the mixture A is smooth and homogeneous and phase B is homogeneous, the emulsion is prepared at ambient temperature by pouring the aqueous phase D onto phase A, by means of a Moritz stirrer.

Once the mixing has been carried out, the stirring is continued until a homogeneous product is obtained and the whole mixture is packaged in a container fitted with a dip applicator corresponding to FIG. 1, the applicator having a form of spatula corresponding to either of FIGS. 19 and 20, the external part (first part) comprising flocking and the second part (central part) being solid without relief. The material used is a Hytrel thermoplastic and the flocking is made of polyamide. The length of the applicator, from the hinge to the longest end, is 20.3 mm, the width L is 6.04 mm and the flocking extends over a strip of approximately 1.3 mm.

The compositions obtained are homogeneous and stable. There is no release (for instance no apparition of a continuous or discontinuous layer of oil) or sedimentation, after treatment in the centrifuge (900 g for 1 hour).

After one week, they do not undergo any phase separation at room temperature or in an oven at 45° C. (more particularly no release (i.e. no apparition of a continuous or discontinuous layer of oil), no sedimentation, no apparition of cracks in the composition).

The viscosity of composition 1 is 1.4 Pa·s and the viscosity of composition 2 is 1.3 Pa·s (Rheomat 180 viscosimeter, spindle 3, 25° C.; 10 minutes, 200 rpm).

The device makes it possible to apply a very thin film to the lips, which is comfortable and which does not stick.

The composition applied does not migrate after one hour and the film wear is satisfactory.

It should be noted that, if a conventional applicator is used for lipgloss (for example a container fitted with a flocked flexible applicator of reference 14030, Geka GmbH), a thicker, stickier deposit is obtained, the resistance of which to migration and to transfer is not as good as when using the applicator according to the invention.

Protocol for Measuring the Film Thickness:

This protocol is an in vitro measurement.

A square of Bioskin® synthetic skin of 3 cm/4 cm is prepared.

The skin square obtained is weighed.

The composition is applied by means of the device so as to obtain an even deposit covering the entire surface of the skin square.

The skin square thus made-up is weighed.

Thickness of the Film:

Thickness (cm)=volume of composition applied (g): density of the composition (g/cm$^3$).

The density of the composition is 1.

The average thickness is given with three separate measurements.

The invention claimed is:

1. A device suitable for applying a cosmetic composition to the lips, comprising:
    an applicator member comprising an applicator head, wherein a portion of the applicator head is flocked and a portion of the applicator head that is not flocked, wherein the applicator head has two opposite faces, the applicator head comprising:
    a first part buying at least one housing, and
    a second part that is connected to the first part by a binge and is at least partially engaged in the housing of the first part, wherein the second part is without a cavity, wherein the first and second parts are both accessible on each of said faces of the applicator head, wherein the applicator head comprises a flocked exterior surround at a distal end,
    a container containing the composition which is in the form of an inverse (water-in-oil) emulsion comprising:
    water:
    an Acrylates/Polytrimethylsiloxy Methacrylate Copolymer film-forming agent:
    at least one polar non-volatile hydrocarbon-based oil; and
    at least one non-volatile phenyl silicone oil free of a dimethicone fragment.

2. The device according to claim 1, wherein the container further comprises a wiping member.

3. The device according to claim 1, wherein the hinge is a film hinge or comprises two flexible strands.

4. The device according to claim 1, wherein the second part is connected to the first part by a hinge disposed on the applicator member away from the distal end of the applicator head.

5. The device according to claim 1, wherein the first part is at least partially flocked.

6. The device according to claim 1, wherein the second part is not flocked or partially flocked, wherein when the second part is partially flocked, the flocking of the first part is different from the flocking of the second part.

7. The device according to claim 1, wherein the second part is engaged entirely in the housing of the first part, being surrounded by the first part.

8. The device according to claim 1, wherein the first part is made of a flexible material.

9. The device according to claim 1, wherein the first and the second part form a single part moulded in a thermoplastic material.

10. The device according to claim 1, wherein the applicator head is attached to a mounting or gripping end piece, the end piece being formed from two half end pieces that are connected together by the binge.

11. The device according to claim 1, wherein the first and the second part are fixed together, when used, in a removable manner by snap-fastening or force-fitting.

12. The device according to claim 1, wherein the at least one polar non-volatile hydrocarbon-based oil is chosen from $C_{10}$-$C_{26}$ alcohols, optionally hydroxylated monoesters, diesters or triesters of a $C_2$-$C_8$ monocarboxylic or polycarboxylic acid and of a $C_2C_8$ alcohol, optionally hydroxylated monoesters, diesters or triesters of a $C_2$-$C_8$ monocarboxylic or polycarboxylic acid and of a $C_2$-$C_8$ alcohol, esters of a $C_2$-$C_8$ polyol and of one or more $C_2$-$C_8$ carboxylic acids, ester oils, vinylpyrrolidone/1-hexadecene copolymers, $C_{12}$-$C_{26}$ fatty acids, dialkyl carbonates, the two alkyl chains being identical or different, and mixtures thereof.

13. The device according to claim 1, wherein the at least one polar non-volatile hydrocarbon-based oil is present in an amount of from 5% to 15% by weight of the composition.

14. The device according to claim 1, wherein the at least one non-volatile phenyl silicone oil is present in an amount from 1% to 8% by weight, relative to the weight of the composition.

15. The device according to claim 1, comprising non-volatile oils in an amount of from 6% to 20% by weight relative to the weight of the composition.

16. The device according to claim 1, wherein the composition further comprises at least one volatile, hydrocarbon-based or silicone oil.

17. The device according to claim 16, wherein the at least one volatile, hydrocarbon-based or silicone oil is present in an amount of from 5% to 45% by weight, relative to the weight of the composition.

18. The device according to claim 1, wherein the water is present in an amount of from 20% to 60% by weight relative to the weight of the composition.

19. The device according to claim 1 wherein the composition further comprises at least one surfactant chosen from non-ionic surfactants and silicone surfactants, or mixtures thereof.

20. The device according to claim 1, wherein the composition has a viscosity at 25° C. of between 0.005 and 12 Pa·s.

21. A process for making up and/or caring for lips in which the composition is applied to the lips by the device according to claim 1.

22. The device according to claim 1, wherein the flocked exterior surround at the distal end extends as a flocked strip forming an O-shaped, a V-shaped or a U-shaped flocked shape.

* * * * *